(12) United States Patent
Porter et al.

(10) Patent No.: US 7,893,177 B1
(45) Date of Patent: Feb. 22, 2011

(54) REDOX POLYMER NANOPARTICLES

(75) Inventors: Marc D. Porter, Ames, IA (US);
Jennifer H. Granger, Northborough, MA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 526 days.

(21) Appl. No.: 11/930,885

(22) Filed: Oct. 31, 2007

Related U.S. Application Data

(60) Division of application No. 11/061,364, filed on Feb. 18, 2005, now Pat. No. 7,309,723, which is a continuation of application No. PCT/US2003/026079, filed on Aug. 19, 2003.

(60) Provisional application No. 60/404,442, filed on Aug. 19, 2002.

(51) Int. Cl.
*C08F 30/04* (2006.01)
*G01N 33/547* (2006.01)

(52) U.S. Cl. .................. 526/240; 526/317.1; 436/531; 436/534; 436/536; 436/538

(58) Field of Classification Search .................. 526/240, 526/317.1; 436/531, 532, 534, 536, 538
See application file for complete search history.

(56) References Cited

U.S. PATENT DOCUMENTS

| | | | | |
|---|---|---|---|---|
| 3,598,850 A | * | 8/1971 | Dewey | 149/19.2 |
| 4,001,194 A | * | 1/1977 | Floyd | 526/240 |
| 5,567,627 A | | 10/1996 | Lehnen | |
| 6,313,334 B1 | * | 11/2001 | Hebekeuser et al. | 556/145 |
| 2006/0003457 A1 | | 1/2006 | Porter et al. | |

OTHER PUBLICATIONS

Watson, K. J., et al., "Hybrid Nanoparticles with Block Copolymer Shell Structures", 121, 462-463(1999).*
*International Search Report*, PCT/US03/26079,(May 4, 2004),2.
"Notice of Allowance mailed Sep. 27, 2007 in U.S. Appl. No. 11/061,364", NOAR,19.
Watson, K. J., et al., "Hybrid Nanoparticles with Block Copolymer Shell Structures", 121, (1999),462-463.

* cited by examiner

*Primary Examiner*—LIng-Siu Choi
(74) *Attorney, Agent, or Firm*—Schwegman, Lundberg & Woessner, P.A.

(57) ABSTRACT

The invention provides nanoparticles and nanoparticle conjugates comprising one or more redox-active species, methods of making nanoparticles and nanoparticle conjugates, and methods for using nanoparticles and nanoparticle conjugates, for example, as diagnostic agents for the detection of various analytes.

20 Claims, 5 Drawing Sheets

REDOX POLYMER NANOPARTICLES

RELATED APPLICATIONS

This application is a divisional application of U.S. patent application Ser. No. 11/061,364, filed Feb. 18, 2005 now U.S. Pat. No. 7,309,723, which is a continuation under 35 U.S.C. 111(a) of PCT/US2003/026079, filed on Aug. 19, 2003 and published in English on Feb. 26, 2004 as WO 2004/016160 A3, which claims priority under 35 U.S.C. 119(e) of U.S. Provisional Application Ser. No. 60/404,442, filed Aug. 19, 2002, which applications and publication are incorporated herein by reference.

FIELD OF THE INVENTION

The invention generally relates to redox-active polymeric nanoparticles and to the use of these materials in diagnostic or detection applications, such as flow cytometry, immunoassays, and flow injection analysis.

BACKGROUND OF THE INVENTION

Pathogen detection and pathogen separation are increasingly important in the diagnosis and treatment of various diseases. Measurement and diagnostic techniques, such as flow cytometry and immunoassay panel tests, are of considerable interest in the assessment of food, water, and environmental quality.

Fluorescent and magnetic polymeric particles have known utility as markers and indicators in various biomedical assays. Among the most commonly used markers for sorting cells are immunoconjugates or immunological labels which include, for example, immunofluorescent and immunomagnetic labels. Immunofluorescent labels typically include, for example, a fluorescent molecule joined to an antibody. Immunomagnetic labels typically include, for example, a superparamagnetic particle joined to either a primary or secondary antibody. Cell labeling can be performed by, for example, attaching the antibody to a marker of interest (e.g., receptor site) on the surface of the cell, that is, a cell surface marker. However, the chemical and physical structure of cell surface marker and density of immunological labels attached to the cell surface can be difficult to accurately determine.

Fluorescent labels can be prepared, for example, by embedding or covalently coupling a fluorescent dye onto a polymeric particle. The resulting fluorescent microparticles can be analyzed manually or by other methods known in the art but preferably using an automated technique, e.g., flow cytometry, such as disclosed in U.S. Pat. No. 4,665,024, to Mansour, et al. The versatility of the fluorescent particles can be further enhanced by the incorporation of multiple fluorescent materials in a single particle. However, while simple absorption of a single dye into a particle can be adequate for most purposes, problems can arise when more than one dye is absorbed into a particle, including: inconsistent emissions attributable to, for example, intermolecular fluorescent energy transfer; differential fluorophore uptake ratios attributable to different dye solubilities within the polymeric matrix; and substrate induced changes in either or both the absorption and emission spectrum of the intercalated fluorophore.

Magnetic particles, such as known magnetically active materials, can be bonded or attached to, for example, antibodies, such as, monoclonal antibodies that are specific to a particular cell type, antigen, or other targets. The resulting magnetic-antibodies can then be mixed with a large population of many different cell types, for example, crude tissue samples, cells grown in a reactor, and the like. The magnetic-antibodies therefore attach only to their pre-selected target cell type, forming a magnetic-antibody-cell conjugate. The conjugate can then be separated from the rest of the cell population using a magnetic field. A shortcoming of magnetic particles is lack of specificity in magnetic labeling in that a cell or other biological target analyte may be rendered paramagnetic by a number of different routes which can confound the analysis and diagnostic information afforded by the method, for example, by binding a specific paramagnetic particle to a specific hapten on a cell or by specific or non-specific binding of a paramagnetic metal or metal complex directly to a cell, such as, a metal binding microorganism or by phagocytosis. Other problems encountered with magnetic particles used in detection and diagnostics include, for example, difficulty in obtaining highly accurate quantification of a cell population's magnetic susceptibility. In addition to their magnetic properties (i.e. magnetic, paramagnetic, and superparamagnetic) magnetic-antibodies can be classified, for example, into three broad categories based on their relative descending size: magnetic particulate labels, colloidal magnetic labels, and molecular magnetic labels, see for example U.S. Pat. No. 6,412,359.

There is currently a need for improved nanoparticulate materials and for methods for detection and analysis therewith, including screening methods which are highly portable for use outside the laboratory setting.

SUMMARY OF THE INVENTION

The present invention provides redox-active polymers and nanoparticles thereof, and methods for their use in, for example, immuno-labeling, recognition schemes, diagnostics, or cell sorting. The methods of the present invention provide advantages which overcome shortcomings of previously existing methodologies.

Accordingly, the invention provides a nanoparticle comprising a polymer that comprises a redox-active species.

The invention also provides a conjugate comprising a nanoparticle of the invention associated with an analyte. The nanopartical and the analyte are typically associated adsorptively, covalently, ionically, hydrophobically, or by hydrogen bonding. In one specific embodiment the nanopartical and the analyte are covalently bonded either directly or through a suitable linking group.

The invention also provides a conjugate comprising a nanoparticle of the invention associated with a labeled-analyte. The nanopartical and the labeled-analyte are typically associated adsorptively, covalently, ionically, hydrophobically, or by hydrogen bonding. In one specific embodiment the nanopartical and the analyte are covalently bonded either directly or through a suitable linking group.

The invention also provides a method for detecting an analyte comprising: contacting a labeled-analyte with a nanoparticle comprising a redox-active species, to form an nanoparticle-labeled-analyte; contacting the resulting nanoparticle-labeled-analyte with a nanoparticle selective cleavant to provide a nanoparticle redox component; and detecting the nanoparticle redox component.

The invention also provides a kit for use in the detection of an analyte, the kit comprising: packaging material comprising a nanoparticle of the invention and instructions regarding how to use the nanoparticle to detect the analyte. The kit can optionally comprise a label reactant capable of specifically binding with the analyte to provide a labeled-analyte; and can also optionally comprise a redox cleavant capable of cleaving the product resulting from the combination of a) the redox polymer nanoparticle and the analyte or b) the redox polymer nanoparticles and the labeled-analyte. The kit can also optionally comprise a signal detector (e.g. chemically modified electrode) capable of detecting a redox signal resulting from cleaving the combination of the nanoparticle, the label reactant, and the analyte.

The invention also provides a process for preparing a polymer comprising reacting a dicarboxylic acid substituted metallocene compound and an organic diol compound to form the polymer. The process can optionally further comprise preparing a nanoparticle that comprises the polymer.

The invention also provides a process for preparing a polymer comprising reacting a difunctional metallocene compound of formula HO-CpFeCp-OH and an organic dicarboxylic acid of formula $HO_2C-R^2-CO_2H$ to provide the polymer. The process optionally further comprises preparing a nanoparticle that comprises the polymer.

The present invention provides polymeric compounds that are highly dispersible or soluble redox polymer nanoparticulate materials, that is redox polymer nanoparticles, which are useful, for example, in improved methods for chemical and biochemical analysis, such as, the detection of biological analytes including micro-organisms or subcellular components. The redox polymer nanoparticles can provide a concentrated packet of redox-active material since the nanoparticles have redox-active materials throughout the nanoparticle and not simply redox-active material as a coating material on an inert supporting particle nor as a redox-active material as a single functional group attached to a label or analyte. The redox-active material of the present invention can be liberated or activated, when desired by, for example, the action of a suitable cleavant which causes the nanoparticle to either or both disassociate from an assembled redox polymer nanoparticle-labeled-analyte conjugate and to degrade the nanoparticle polymer. An example is the polymer in formula (I) (shown herein below) which affords a readily detectable redox product or component, such as an Fe(II) ion or a complex thereof, such as the iron (II) ferrozine complex.

The nanoparticulate materials of the present invention also have application in diagnostic kits or assays, such as immunoassays, in improved imaging agents, in purification processes, in drugs, for example, treatment regimes and therapies, such as drug delivery to specifically target and shrink tumors or to identify and separate infectious agents, and the like.

The present invention also provides a composition comprising a polymer nanoparticle having a polymer matrix and a redox-active species in the polymer matrix.

The present invention also provides a method for preparing nanoparticles comprising a polymer of the invention comprising polymerizing, for example, an emulsion of a difunctional ferrocene compound, such as a dicarboxy substituted ferrocene compound, a di-functional spacer compound, such as an diol or polyol compound, and optionally a catalyst.

The present invention also provides a redox article comprising an analyte having attached to the analyte a label (e.g. antibody) to form a "labeled-analyte", and a redox polymer nanoparticle attached to the label portion of the "labeled-analyte" to provide an association or conjugate referred to as a "redox polymer nanoparticle-labeled-analyte".

The present invention also provides a method for detecting an analyte comprising: contacting a redox polymer nanoparticle-labeled-analyte with a redox polymer nanoparticle selective cleavant; and detecting a nanoparticle redox component.

The present invention also provides a method for detecting an analyte comprising:

contacting a labeled-analyte with a redox polymer nanoparticle to form a redox polymer nanoparticle-labeled-analyte;

contacting the resulting redox polymer nanoparticle-labeled-analyte with a redox polymer nanoparticle selective cleavant; and detecting a nanoparticle redox component.

The present invention also provides an assay kit for use in the detection of an analyte, the kit comprising:

a redox polymer nanoparticle capable of specifically binding with a labeled-analyte;

optionally a label reactant capable of specifically binding with an analyte of interest and the redox polymer nanoparticle; and optionally a redox cleavant capable of cleaving a "redox polymer nanoparticle-labeled-analyte", that is the product resulting from the combination of the redox polymer nanoparticles, the label reactant, and the analyte.

The present invention also provides a method of preparing analytes labeled with redox polymer nanoparticles by, for example, coupling (e.g. covalently) or any other known method(s) of associating the redox polymer nanoparticles directly to the analyte (e.g., through ionic bonds, hydrogen bonds, by simple adsorption or entrapment), or indirectly to the analyte, for example, attaching the redox polymer nanoparticle to an intermediate or intervening "label" entity, such as a antibody or other suitable entity which is already attached to the analyte or can thereafter be attached to the analyte.

The present invention provides methods to detect and analyze various analytes which can include, for example, biological and non-biological materials, such as bio-molecules, polymers, particulates, and like target analytes, and as illustrated herein.

The invention also provides synthetic intermediates, polymers, and synthetic methods disclosed herein that are useful for preparing nanoparticles of the invention.

Other objects of the invention will be apparent to those of ordinary skill in the art in view of the disclosure provided herein.

DETAILED DESCRIPTION OF THE INVENTION

Figure 1A:
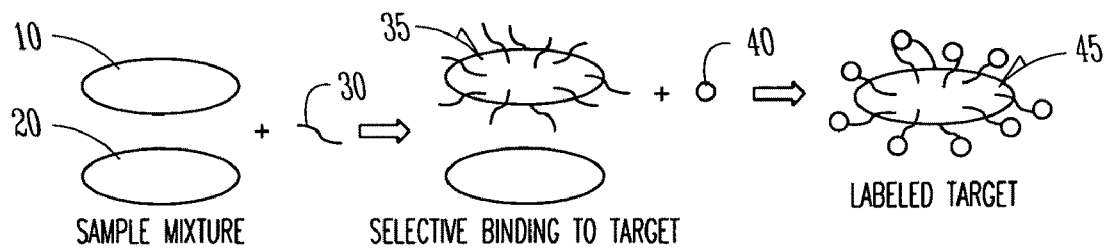
FIG. 1A schematically illustrates an example nanoparticle-labeled-analyte labeling scheme of the present invention.

Applicants have discovered that polymers of the invention and nanoparticles comprising such polymers are useful for labeling, detection, identification, and like applications, of various biological and non-biological analytes. The redox-active species can be dispersed through the polymer matrix, can be appended to the backbone of the polymer, or can be incorporated directly into a polymer backbone. When the redox-active species is appended to the polymer it can be bonded to the polymer as a side chain or side group, but is not part of the polymer backbone. Preferably, the agent is bonded to the polymer through a linkage that is suitable to release the agent when desired. For example, it can be bonded through a group that includes a linkage that can broken by thermal, chemical, or photolytic means. For example, the redox-active species can conveniently be linked to the polymer through a hydrolyzable linkage.

When the redox-active species is "dispersed through the polymer matrix" it is located within the matrix of a polymer, but is not bonded to the polymer. Preferably, it is dispersed in a manner such that it can be released in a controlled fashion. The redox-active species can be introduced into the matrix of the polymer by any suitable method. For example, the polymer can be contacted with a solution of the species under conditions suitable for the species to enter into the matrix of the polymer. Polymers having a redox-active species dispersed in the polymer matrix can also be prepared by polymerization of one or more monomers in the presence of the redox-active species, so that the species becomes dispersed in the polymer matrix during polymer formation.

In embodiments the nanoparticles of the invention can be prepared by, for example, a process comprising contacting a di-functional metallocene compound and a di-functional spacer compound which can produce a copolymeric product of the di-functional metallocene compound and a di-functional spacer compound. Specifically, the present invention provides a polymer prepared by the process comprising reacting a dicarboxylic substituted ferrocene compound and an organic diol compound to provide, for example, the polymer of formula (I)

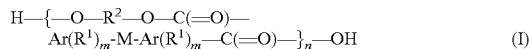

wherein:

M is complexed Fe;

Ar is an unsubstituted or substituted cyclopentadienyl (Cp) complexed to M;

each $R^1$ is independently a cyclopentadienyl substituent selected from —OH, $(C_{1-7})$alkoxy, $(C_{1-7})$alkyl, substituted $(C_{1-7})$alkyl, poly{substituted $(C_{1-7})$alkyl}, $(C_{1-7})$alkanoyl, aryl, or substituted aryl;

$R^2$ is $(C_{1-7})$alkenyl, substituted $(C_{1-7})$ alkenyl, poly{substituted $(C_{1-7})$ alkenyl}, cyclo$(C_{3-7})$alkenyl, aryl $(C_{1-7})$alkenyl, $(C_{1-7})$alkenylaryl, or aryl$(C_{1-7})$alkenylaryl;

m is independently 0 to 4; and n is 3 to about 1,000;

or a salt thereof.

In embodiments the nanoparticles of the invention can be isolated from the reaction mixture of, for example, a di-functional metallocene (e.g. ferrocene) compound of the formula A-CpMCp-A (wherein M is a metal), and a di-functional spacer compound of the formula B—$R^2$—B, where A and B are co-reactive functional groups capable of reacting with each other to form a copolymer, as illustrated in the following scheme.

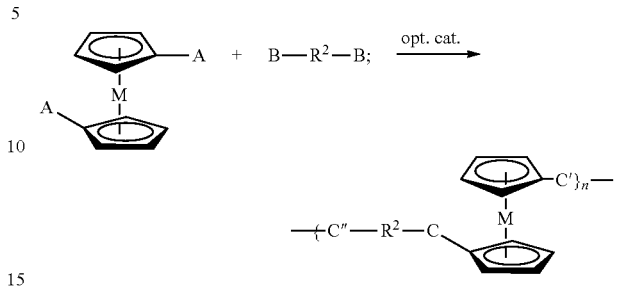

For example, a polyester wherein C is —O—C(=O)—, C' is —C(=O)—, and C" is —O— can be formed from such monomers, wherein each A is a carboxylic acid —$CO_2H$ and each B is a hydroxyl group —OH.

Co-reactive groups A and B as well as methods for reacting such groups to provide polymers are known. For example, the following table illustrates co-reactive groups A and B that can be used to prepare a polymer of the invention having repeating units of formula -D-$R^2$-D-Ar($R^1$)$_m$-M-Ar($R^1$)$_m$—

| Reactive Group A | Reactive Group B | Resulting Linkage In Polymer D |
| --- | --- | --- |
| —COOH | —OH | Ester |
| —COOH | —NHR | Amide |
| —OH | —COOH | Ester |
| —NHR | —COOH | Amide |
| —COOH | —COOH | Anhydride |
| —NCO | —OH | Urethane |
| —OH | —NCO | Urethane |
| —NCO | —NHR | Urea |
| —NHR | =NCO | Urea |
| —OH | —OH | Ether |

A preferred di-functional ferrocene compound of the formula A-CpMCp-A is dihydroxy ferrocene, a preferred a di-functional spacer compound of the formula B—$R^2$—B is 1,6-hexane dicarboxylic acid, a preferred M is Fe, and a preferred optional catalyst is para-toluene sulfonic acid. Other co-polymerization, monomer-monomer coupling, cross-linking, metathesis, and like synthetic methods are known in the art and are generally applicable to the preparation of the polymers or copolymers of the formula (I). These methods can also optionally be used to form associations or conjugates of nanoparticle, label, and analyte components, see for example, Feiser and Feiser, "Reagents for Organic Synthesis", Vol. 1, 1967, et seq.; March, J., "Advanced Organic Chemistry", John Wiley & Sons, 4 ed. 1992; House, H. O., "Modern Synthetic Reactions", $2^{nd}$ ed., W. A. Benjamin, New York, 1972; and Larock, R. C., "Comprehensive Organic Transformations", $2^{nd}$ ed., 1999, Wiley-VCH Publishers, New York, Specifically, the present invention provides a polymer of formula (I) isolated from the reaction mixture of a dicarboxylic substituted ferrocene compound and an organic diol compound.

In embodiments a method for preparing nanoparticles of the polymer of the invention comprises polymerizing, such as an emulsion, of a di-functional ferrocene compound or other metallocenes, a di-functional spacer compound, and optionally a catalyst. The di-functional ferrocene compound can be, for example, ferrocene dicarboxylic acid and the di-functional spacer compound can be, for example, an organic diol, such as ethylene glycol, 1,6-hexane diol, polyalkylene oxides polyalkylene or glycols, such as poly(ethylene) oxides, and like diols and polyols. The polymerizing can be accomplished by, for example, heating about 1 molar equivalent of the di-functional ferrocene compound, about 1 to about 2 molar equivalents of the di-functional spacer compound, and optionally an emulsifier, such as a surfactant, in a suitable aqueous media, such as water, aqueous buffered media, mixtures of water and water miscible or immiscible solvents, or combinations thereof. An organic acid can be selected as a polymerization catalyst when, for example, the co-monomers produce ester linkages as in a polyester polymer or copolymer. A suitable organic acid as a polymerization catalyst is, for example, para-toluene sulfonic acid (p-TSA) and like protic acids. Depending on the selection of monomers, solvent, extent of polymerization, an like considerations, the resulting polymer product can be soluble or highly dispersible discrete particles in the reaction media. Alternatively, the resulting polymer product can be insoluble in the reaction media so as to form an insoluble separate phase which can be useful in isolation, purification, or formulation schemes of the polymer product as redox polymer nanoparticles.

Other metallocene compounds are known, such as ruthenocene, cobaltocene, nickelocene, which can be used in embodiments of the present invention, see "Basic Inorganic Chemistry" by F. Albert Cotton, Geoffrey Wilkinson, and Paul L. Gaus, John Wiley and Sons, Inc., 3rd Ed., 1995. Embodiments of the present invention can be adapted to other types of nanoparticles containing redox active polymeric materials, such as viologens, catechols, and like compounds, see Murray, R. W., "Chemically Modified Electrodes."[1]

The resulting nanoparticles prepared in processes of the present invention can have average particle diameters, for example, of at least about 10 nanometers. In one embodiment of the invention the nanoparticles of the invention can have average particle diameters of from about 10 to about 1,000 nanometers, preferably of from about 10 to about 100 nanometers, and more preferably of from about 10 to about 20 nanometers. The size of the nanoparticles for use in embodiments of the present can be selected based on the number of particles that can be attached to the analyte and the sensitivity of the electrochemical detection scheme selected.

The present invention provides redox-active polymer nanoparticles. The nanoparticles can, if desired, be formed in situ during, or subsequent to, the polymerization or copolymerization of polymerizable monomer components by, for example, emulsion, micro-emulsion, mini-emulsion, micellar, vesicular, and like polymerization systems.

The resulting redox polymer nanoparticles can optionally contain additional surface functional groups, for example, hydrophilic groups or hydrophobic groups, such as carboxylates, esters, alcohols, carbamides, aldehydes, amines, sulfur oxides, nitrogen oxides, halides, and like groups which can be used to facilitate or manipulate nanoparticle properties, for example, nanoparticle dispersion, nanoparticle stability, redox properties, such as the reversibility of the redox process and redox potentials, or particle-to-particle aggregation, and the attachment of analytical reactants. Optional surface functional groups can be introduced into the redox polymer nanoparticle products by, for example, judicious selection of the monomer or co-monomer(s) prior to polymerization, by modification of existing functional groups (e.g. deprotection of protecting groups), or by attachment to the polymer or nanoparticles formed therefrom subsequent to polymerization. The redox polymer nanoparticles can be in particulate form and formed from a polymer of formula (I) having an average particle diameter of, for example, from about 1 nanometer to about 10,000 nanometers. The redox polymer nanoparticles of the present invention can be attached directly to the analyte. Alternatively, the nanoparticles can be attached to a label entity, i.e. intervening spacer entity, and the label entity is in turn attached to the analyte.

The analyte can be a variety of molecular or particulate entities including but not limited to, for example, biologicals, such as, a microorganism, a virus, a cell, a cell component, an antigen, an antibody, a receptor, a hapten, an enzyme, a hormone, a pathogen, a toxin, a biopolymer, for example, a protein, a glycoprotein, a carbohydrate, a peptide, a nucleic acid, a synthetic polymer, a chemical compound, such as a small or large drug molecule, therapeutic agent, or metabolite, and like entities, or combinations thereof. When the analyte is a discrete particle or particulate entity it can have particles having diameters, for example, of about 0.1 to about 1,000 micrometers. The analyte can further include, if desired, a fluorescent compound, a magnetic particle, or combinations thereof. The analyte can be, for example, a compound, polymer, complex, aggregation, or composition to be detected and measured, which is mono- or polyvalent, that is, having one or a plurality of determinant sites, haptenic and antigenic, a single compound or plurality of compounds which share at least one common epitopic or determinant site; or a receptor. It will be evident to one skilled in the art that "analyte" as used in the present invention can include "label" or "labeled-analyte" as defined herein.

The "label" can be or include, for example, an antibody, an antibody fragment, a fluorescent compound, a magnetic particle, hybridized nucleic acid, and like materials, and combinations thereof.

A "labeled-analyte" can be produced, in situ or ex situ, by attaching any label, which is analyte selective, to any suitable analyte such as the above-mentioned molecular or particulate entities, including but not limited to, for example, biologicals, bio- or synthetic polymers, a chemical compound, and like entities, or combinations thereof. In embodiments the label can be attached to the analyte and the nanoparticle is attached to the label. In other embodiments the label and the nanoparticle can be attached to the analyte. The redox nanoparticles can be attached to the analyte or the label, for example, adsorptively, covalently, ionically, hydrophobically, via hydrogen bonding, and like associations, or combinations thereof.

The present invention provides a method for detecting an analyte comprising:

contacting a labeled-analyte with a redox polymer nanoparticle to form a redox polymer nanoparticle-labeled-analyte;

contacting the resulting redox polymer nanoparticle-labeled-analyte with a redox polymer nanoparticle selective cleavant to provide a nanoparticle redox component; and detecting the nanoparticle redox component.

In one embodiment, the invention provides a nanoparticle comprising a polymer that comprises one or more units of formula (III):

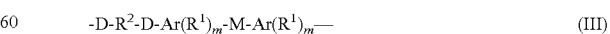    (III)

wherein: M is a complexed metal atom or metal ion; Ar is unsubstituted or substituted arenyl or aromatic group complexed to M; each $R^1$ is independently an arenyl substituent or aromatic substituent selected from —OH, $(C_{1-7})$alkoxy, $(C_{1-7})$alkyl, substituted $(C_{1-7})$alkyl, poly{substituted $(C_{1-7})$alkyl}, $(C_{1-7})$alkanoyl, aryl, —$(OCR^3CH_2)_o$—, or substituted aryl; $R^2$ is $(C_{1-7})$alkenyl, substituted $(C_{1-7})$ alkenyl, poly{substituted $(C_{1-7})$ alkenyl}, cyclo$(C_{3-7})$alkenyl, aryl $(C_{1-7})$alkenyl, $(C_{1-7})$alkenylaryl, —(OCR$^3$CH$_2$)$_p$—, or aryl $(C_{1-7})$alkenylaryl; each D is independently —O—, —OC (=O)—, —C(=O)O—, —NR$_a$C(=O)—, —C(=O) NR$_a$—, —OC(=O)O—, —NR$_a$C(=O)NR$_a$—, —OC(=O) NR$_a$—, —NR$_a$C(=O)O—, —C(=O)—OC(=O)— —CH$_2$CH$_2$—, or —CH=CH—; each R$_a$ is independently H or $(C_{1-7})$alkyl; m is independently 0, 1, 2, 3, or 4; each $R^3$ is independently —H or $(C_{1-7})$ alkyl; o is 1 to about 10; and p is 1 to about 50. An another embodiment the invention provides a nanoparticle comprising a polymer that comprises 2 or more repeating units of formula (III). In another embodiment, formula (III) has the formula:

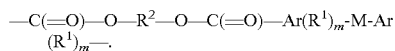

In another embodiment formula (III) has the formula:

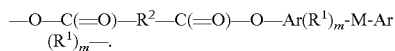

In yet another embodiment, formula (III) has the formula:

In one embodiment, the invention provides a nanoparticle comprising a polymer having formula (I):

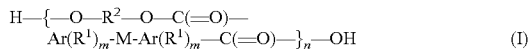

wherein: M is a complexed metal atom or metal ion; Ar is unsubstituted or substituted arenyl or aromatic group complexed to M; each $R^1$ is independently an arenyl substituent or aromatic substituent selected from —OH, $(C_{1-7})$alkoxy, $(C_{1-7})$alkyl, substituted $(C_{1-7})$alkyl, poly{substituted $(C_{1-7})$ alkyl}, $(C_{1-7})$alkanoyl, aryl, —(OCR$^3$CH$_2$)$_o$—, or substituted aryl; $R^2$ is $(C_{1-7})$alkenyl, substituted $(C_{1-7})$ alkenyl, poly{substituted $(C_{1-7})$ alkenyl}, cyclo$(C_{3-7})$alkenyl, aryl $(C_{1-7})$alkenyl, $(C_{1-7})$alkenylaryl, —(OCR$^3$CH$_2$)$_p$—, or aryl $(C_{1-7})$alkenylaryl; m is independently 0 to 4; n is 3 to about 1,000; each $R^3$ is independently —H or $(C_{1-7})$ alkyl; o is 1 to about 10; and p is 1 to about 50.

In one embodiment the invention provides a nanoparticle comprising a polymer having formula (I):

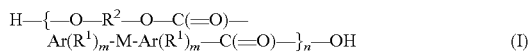

wherein: M is a complexed metal atom or metal ion; Ar is unsubstituted or substituted arenyl or aromatic group complexed to M; each $R^1$ is independently an arenyl substituent or aromatic substituent selected from —OH, $(C_{1-7})$alkoxy, $(C_{1-7})$alkyl, substituted $(C_{1-7})$alkyl, poly{substituted $(C_{1-7})$ alkyl}, $(C_{1-7})$alkanoyl, aryl, or substituted aryl; $R^2$ is $(C_{1-7})$ alkenyl, substituted $(C_{1-7})$ alkenyl, poly{substituted $(C_{1-7})$ alkenyl}, cyclo$(C_{3-7})$alkenyl, aryl$(C_{1-7})$alkenyl, $(C_{1-7})$alkenylaryl, or aryl$(C_{1-7})$alkenylaryl; m is independently 0 to 4; and n is 3 to about 1,000.

In one embodiment $R^1$ is of the formula -(OCR$^3$CH$_2$)$_o$— OR$^3$, where $R^3$ is —H or —CH$_3$, and o is 1 to about 10.

In one embodiment $R^2$ is of the formula —(OCR$^3$CH$_2$)$_p$—.

In one embodiment —Ar(R$^1$)$_m$-M-Ar(R$^1$)$_m$— is a divalent ferrocene.

In one embodiment the invention provides a nanoparticle comprising a polymer having formula (I):

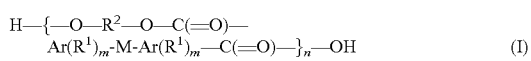

wherein: M is a complexed metal atom or metal ion; Ar is unsubstituted or substituted arenyl or aromatic group complexed to M; each $R^1$ is independently an arenyl substituent selected from —OH, $(C_{1-7})$alkoxy, $(C_{1-7})$alkyl, substituted $(C_{1-7})$alkyl, poly{substituted $(C_{1-7})$alkyl}, $(C_{1-7})$alkanoyl, aryl, or substituted aryl; $R^2$ is $(C_{1-7})$alkenyl, substituted $(C_{1-7})$ alkenyl, poly{substituted $(C_{1-7})$ alkenyl}, cyclo$(C_{3-7})$alkenyl, aryl$(C_{1-7})$alkenyl, $(C_{1-7})$alkenylaryl, or aryl$(C_{1-7})$alkenylaryl; m is independently 0 to 4; and n is 3 to about 1,000; or a salt thereof.

A preferred redox polymer nanoparticle of the present invention is poly(1,1'-dihexylferrocenyl)ester (PDE) which is formed during emulsion polymerization as illustrated herein. A preferred redox product or component is formed from disintegration, such as by aqueous acidic hydrolysis, of poly (1,1'-dihexylferrocenyl) ester nanoparticles in the methods of use of the present invention is Fe (II) ion or a complex thereof, such as the iron (II) ferrozine complex, or the like complexes.

Other preferred products can include, for example, products formed in post-disintegration reaction, such as, inorganic complexation products or chemical reaction products such as iron sulfides, see U.S. Pat. No. 6,048,920. Disintegration as used herein can indicate, for example, partial or complete breakdown of the nanoparticle, its molecular constituents, or its associations or conjugations with a label or an analyte, into smaller constituents, such as, individual constituents, molecular fragments of the compound of formula (I), and a detectable ion. A preferred apparatus and method for contacting and detecting redox components formed in methods of the present invention is "electrochemical flow cytometer", that is, a flow cytometer equipped, for example, with a chemically modified electrode using flow cytometry, for example, on a chip-scale device. Other detection methods known to those skilled in the art can also be selected.

The nanoparticle selective redox cleavant can be, for example, an aqueous mineral acid, such as, hydrochloric acid, sulfuric acid, nitric acid, phosphoric, and like acids, or organic acids, such as, trichloroacetic acid, acetic acid, formic acid, and like acids, and combinations of either or both mineral acids and organic acids. It will be evident to one of ordinary skill in the art that metallocene complexes selected for use in embodiments of the present invention can be, alternatively or additionally, selectively cleaved with other agents, for example, enzymatically, such as amide bonds of amino acid linkages, photo-chemically, such as by exposure to ultraviolet or other suitably energetic radiation, or by oxidation(s) or reduction(s), such as, by electrochemical redox methods, exposure to oxidants, such as, oxygen, or reducing agents, such as NaBH$_4$, and combinations of agents. An example of oxidizable or reducible linkages are disulfide (—S—S—) bonds. Other suitable reactive linkages for the cleavant to act on include, but are not limited to, for example, esters, thioesters, ethers, polyethers, carbonates, and like cleavable functional groups including suitable protecting groups.

Specifically, the redox cleavant, preferentially and preferably exclusively, cleaves or disintegrates, that is, liberates the redox polymer nanoparticle from its association or conjugation with the analyte or labeled-analyte, and preferably simultaneously produces a detectable species, such as a metal ion, from degradation of the metallocene portion of the metallocene containing polymer which comprises the redox polymer nanoparticle. The cleavant generally acts on the product resulting from the combination of the redox polymer nanoparticles, the label reactant, and the analyte, to produce a product that has, or can be converted to, a species having a distinctive and readily detectable signal, such as electrochemically.

The present invention provides a method for determining the presence or absence of an analyte in a sample, comprising:

mixing the sample and known amounts of a label whereby the label selectively attaches to the analyte to form a first reaction mixture comprising a labeled-analyte;

contacting the first reaction mixture with a redox polymer nanoparticle whereby the redox polymer nanoparticle selectively attaches to the labeled-analyte to form a second reaction mixture comprising a redox polymer nanoparticle-labeled-analyte, contacting the second reaction mixture containing the redox polymer nanoparticle-labeled-analyte with a redox polymer nanoparticle cleavant to provide a third reaction mixture; and analyzing the resulting third reaction mixture for any redox component from cleaving the redox polymer nanoparticle-labeled-analyte to establish the presence or absence of the analyte in the sample.

The contacting of the resulting second reaction mixture and analyzing can be accomplished, for example, within a flow cytometer equipped with a chemically modified electrode. The method can further include correlating the amount of redox component liberated (by treatment with the selective cleavant) with the amount of analyte present in the sample, for example, with a reference standard, and for example, a calibration curve. The above method for determining the presence or absence of an analyte in a sample can be accomplished with any of the above mentioned analytes, labels, or redox polymer nanoparticles, and combinations thereof. In embodiments, the nanoparticles and analytical methods thereof of the present invention can be used effectively without need for nanoparticle disintegration or digestion, for example, when in the nanoparticle or its association or conjugation products can be detected by alternative methods, such as spectroscopically.

For detection or quantitation of a target analyte, a sample is combined with a label which associates or reacts with the analyte. The resulting labeled-analyte conjugate can optionally be separated, for example, by filtration, fractionation, and like methods, from any unbound components of the sample before being combined with known amounts of a redox polymer nanoparticle. The resulting nanoparticle-labeled-analyte conjugate can also optionally be separated from any unbound components of the sample and before further analysis of the product. If desired, another useful separation method or association method for forming conjugates or adducts useful in embodiments of the present invention is based on molecular affinity, such as affinity chromatography, whereby specific immobilizing or associative molecular interactions occur between an analyte or molecules of interest within a sample mixture and another component such as a label or nanoparticle supported ligand component to permit selective separation of the analyte from other materials in the sample by first eluting non-immobilized material and then subsequently washing or flushing the analyte of interest from the supported ligand.

Detecting the resulting nanoparticle redox component(s) can be accomplished using any acceptable method, for example, with a chemically modified electrode. The detected nanoparticle redox component can be, if desired, correlated to the amount and the type of analyte in the original sample.

Methods for detection and analysis include but are not limited to, for example, known fluorometers, magnetometers, epifluorescence microscopes, scanning microscopes, confocal microscopes, and capillary electrophoresis detectors. Methods for signal amplification can also be used and include, for example, known methods which boost a signal, directly or indirectly, which signal is representative of the target analyte such as a filter which can increase the signal-to-noise ratio of electrode selected for detecting the redox component of the nanoparticles associated with and liberated from an analyte. A preferred method to detect, differentiate, sort, quantitate, analyze, and like aspects of analytes or portions of analytes in a sample is the above mentioned "electrochemical flow cytometry".

Many methods exist for detecting various analytes of interest. Suitable detecting methods useful in the present invention can involve using one or more signal producing systems in addition to the above mentioned electrochemical detection of the redox component of the redox polymer nanoparticles. The labeled-analyte or redox polymer nanoparticle-labeled-analyte conjugates of the present invention can be detected either directly or indirectly, or both. Alternative detection methods can include the use of, for example, dyes, enzymes, enzyme substrates or co-factors, enzyme inhibitors, fluorescers, chemiluminescers, particles, and the like, and combinations thereof.

The present invention provides a kit for use in the detection of an analyte, the kit comprising packaging material comprising a redox-active polymer of the invention and instructions regarding how to use the redox-active polymer to detect the analyte.

The invention also provides a kit for use in the detection of an analyte, the kit comprising packaging material comprising 1) a redox polymer nanoparticle of the invention that is capable of specifically binding with the analyte or with a labeled-analyte, 2) instructions regarding how to use the redox-active polymer nanoparticle to detect the analyte, 3) optionally a label reactant capable of specifically binding with the analyte to provide a labeled-analyte, 4) and optionally a redox cleavant capable of cleaving the product resulting from the combination of a) the redox polymer nanoparticle and the analyte or b) the redox polymer nanoparticles and the labeled-analyte.

The present invention provides a kit for use in the detection of an analyte, the kit comprising:

any redox polymer nanoparticle material capable of specifically binding with a labeled-analyte, such as those mentioned above;

optionally a label reactant capable of specifically binding with an analyte of interest and the redox polymer nanoparticle; and optionally a redox cleavant capable of cleaving the product resulting from the combination of the redox polymer nanoparticles, the label reactant, and the analyte.

The kit can further include if desired, for example, a known signal detector capable of detecting and optionally amplifying a redox signal resulting from cleaving the combination of the redox nanoparticle, the label reactant, and the analyte, such as a chemically modified electrode, ion selective electrode, and like electrode detectors. The kit can, if desired, include a reference material which can be essentially identical to the analyte in binding affinity or properties with either or both the label reactant and the redox polymer nanoparticle.

The redox polymer nanoparticles of the present invention have applications in, for example, diagnostic kits, drug delivery, imaging agents, and in detection, identification, and purification processes, such as cell sorting processes. Cell sorting processes are known and have been use to sort or separate different cells in a mixed population of cells, e.g., pathogens, cancerous vs. normal cells, sperm bearing chromosomes for male versus female, and like applications. The redox polymer nanoparticles of the present invention, alone or in combination with another entity, such as a label or a linker, can also be used to identify and differentiate different cell lines or cell types and to facilitate the cell sorting process. Automated means of cell sorting are known and include "biochips" which use controlled electrical fields to collect specific cell types onto electrodes in the biochip. Other sorting machines and methods include, for example, fluorescence-activated cell sorters (FACs), magnetic particle-antibody sorters, and the like.

The redox polymer nanoparticles of the present invention can function analogously, but not identically, to the above mentioned fluorescent micro-particles or fluorescent compounds in the above mentioned fluorescent bioassays such as FACs. However, in the present invention the redox active polymer nanoparticles can be, if desired, controllably chemically disintegrated to produce a redox active metal ion species, such as, Fe (II) when the nanoparticle is obtained from, for example, a polymerization including substituted ferrocene monomers. The presence of the liberated species is a readily detected by using conventional electrochemical techniques, for example, cyclic voltammetry, amperometry, or potentiometry. Additionally, the present invention enables separation or sorting schemes, for example, to separate specific desired cells from a large population of other or different cells in a sample mixture by, for example, modifying a target analyte cell in a cell population with either or both a label and a redox polymeric nanoparticle of the present invention, and thereafter liberating and detecting the electroactive metal ion species in a separation scheme, such as, in a electrochemical flow cytometer as illustrated herein.

"Micro-particles" are small particles with overall diameters in the micrometer range. "Nanoparticles" refer to smaller particles with overall discrete diameters approximately in the nanometer range. "Nanoparticles" of the present invention designate a particulate material in the nanometer range and which material can be either soluble or insoluble depending upon, for example, the surrounding media, whether the nanoparticle is associated with another entity such as a label or target analyte, and like considerations. Preferably the nanoparticles of the present invention are soluble in the surrounding media, for example, a reaction mixture such as an aqueous buffer or a carrier liquid, such as blood plasma.

Because of the small size and uniformity of the redox polymer nanoparticles of the present invention and their apparent solubility or dispersibility properties, the nanoparticles preferably provide polymeric "molecular labels" which can readily transport and associate with or be bonded to another entity, such as a second label entity or a target analyte on a molecular level. The nanoparticles can be associated with a biological target material, for example, a microorganism, or a surface modified biological target material, such as a micro-organism having a fluorescent label or magnetic label appended to the surface of the microorganism. The association enables useful analytical detection, diagnostic, or differentiation schemes.

The present invention provides redox polymer nanoparticles which are made of polymeric or copolymeric materials which include but is not limited to at least one first polymerizable metallocene monomer, such as a divinyl substituted ferrocene, a 3,3'-dihydroxy substituted ferrocene, i.e. a ferrocene diol, or ferrocene dicarboxylic acid, and optionally a second polymerizable monomer, such as an olefin, dicarboxylic acid, or diol, and which second polymerizable monomer is copolymerizably compatible with the polymerizable metallocene monomer.

The redox polymer nanoparticles of the present invention comprising a polymer nanoparticle having a polymer matrix and a redox active species in the polymer matrix can also be prepared by, for example, particle growth and encapsulation, such as dissolving a suitable matrix polymer in a suitable solvent containing a soluble redox active species followed by, for example, differential evaporation, trituration, concentration or like techniques, to control or limit the particle size growth to the nanometer domain. Another alternative preparative method uses suspended porous preformed polymer nanoparticles wherein the nanoparticles are imbibed or impregnated with a suitable solution containing a redox active specie.

The redox-active species can be any redox-active material that can be incorporated into a nanoparticle of the invention. For example, the term redox-active species includes organic redox couples (e.g. viologens, quinines, and hydroquinines), organometallic materials (e.g. metallocenes), and inorganic materials (e.g. Ruthenium hexamine or Indium hexachloride). In embodiments the redox-active species can be, for example, a metal or a metal ion of any suitable element, such as Cu, Ag, Au, Sn, Fe, Ni, Ru, Ti, Ta, Nb, Hf, W, Y, Zn, Zr, Al, La, Ce, Pr, Nd, Sm, Sb, Bi, Pb, Ti, In, Te, Cr, V, Mn, Mo, Co, Rh, Pd, Pt, Cd, Os, Re, Ir, Hg, and mixtures thereof. It is readily evident to one skilled in the art that the redox active species can also be an oxide, a salt, or an organo- or inorganic complex, of any suitable element. It is readily evident to one skilled in the art that the redox active species can also be electrodeposited and optionally stripped or reoxidized using known electrochemical methods to provide additional or alternative detection modes.

Suitable polymeric materials for use as, for example, labels, copolymer spacer groups, polymer micro-particles, or polymer nano-particles, such as the matrix polymer, in the present invention include but are not limited to, for example, polystyrene, halogenated polystyrene, polyacrylic acid, polyacrylonitrile, polyamide, polyacrylamide, polyacrolein, polybutadiene, polycaprolactone, polycarbonate, polyester, polyethylene, polyethylene terephthalate, polydimethylsiloxane, polyisoprene, polyurethane, polyvinylacetate, polyvinylchloride, polyvinylpyridine, polyvinylbenzylchloride, polyvinyltoluene, polyvinylidene chloride, polydivinylbenzene, polymethylmethacrylate, polylactide, polyglycolide, poly(lactide-co-glycolide), polyanhydride, polyorthoester, polyphosphazene, polyphosophaze, polysulfone, and like polymers, mixtures thereof, or combinations or copolymers thereof. Other alternative polymer materials, natural or synthetic, such as carbohydrates, e.g., carboxymethyl cellulose, hydroxyethyl cellulose, agar, gel, proteinaceous polymer, polypeptide, eukaryotic and prokaryotic cells, viruses, lipid, metal, resin, latex, rubber, silicone, such as polydimethyl siloxane, glass, ceramic, charcoal, kaolinite, bentonite, and like materials or entities can also be used as or incorporated into the redox polymer nanoparticles. The terms "first", "second", etc. as applied to monomer or polymer species of nanoparticles, are used for the purposes of identification only and do not imply any order of preference.

The redox polymer nanoparticles of the present invention can optionally be prepared with a known cross-linking agent to, for example, control or alter the disassociation or disintegration properties of the redox polymer nanoparticles in, for example, the diagnostic or detection stages of the methods of use. Cross-linking agents are, for example, divinyl benzene, ethylene glycol dimethacrylate, trimethylol propane trimethacrylate, N,N'-methylene-bis-acrylamide, alkyl ethers, sugars, peptides, DNA fragments, or other known functionally equivalent agents. It is readily evident to one skilled in the art that many cross-linking agents can be used with, or are interchangeable as the second polymerizable monomer with, the first polymerizable metallocene monomer or functionally related monomer.

In a preferred embodiment the analyte is a microparticle including a cellular entity such as a particular infectious microorganism within a population of microorganisms, such as bacteria, or a particular blood cell type such as sickle cells in a blood sample; a label can be antibody or antibody fragment which is highly specific and selective for the targeted or "matched" cellular entity; and redox polymer nanoparticles are made of copolymeric polyesters of a metallocene monomer and a second monomer.

The redox polymer nanoparticle of the present invention can be selectively linked to either or both a label material and analyte by, for example, any known chemical coupling reactions such as carbodiimide coupling. Other coupling methods include use of carboxylates, esters, alcohols, carbamides, aldehydes, amines, sulfur oxides, nitrogen oxides, or halides, and other methods known in the art can be used. Coupling, for example, a nanoparticle to a label, a labeled-analyte to nanoparticle, a nanoparticle to an analyte, a labeled-nanoparticle to an analyte and like combinations, can generally be accomplished by applying the procedures and principles disclosed in U.S. Pat. No. 6,268,222, or other procedures known in the art as applied to the novel materials and their combinations of the present invention.

The redox polymer nanoparticles of the invention, alone or in combination with a label, can be used for passive or covalent coupling of biological material, i.e., an analyte, such as haptens, antigens, antibodies, enzymes or nucleic acids, and used for various types of analyte assays such as immunoassays, nucleic acid (DNA or RNA) assays, affinity purification, cell separation, and other medical, diagnostic, environmental, and industrial applications.

The nanoparticles can optionally incorporate known magnet or magnetically responsive materials, such as, superparamagnetic, paramagnetic, ferromagnetic metal oxide, and combinations thereof. The nanoparticles can optionally incorporate known fluorescently responsive materials, such as, dyes, pigments, and combinations thereof. The nanoparticles can optionally incorporate either or both of the above mentioned magnet or fluorescently responsive materials to provide electrochemically responsive materials of the present invention which can also optionally be adapted to be magnetically active, fluorescently active, and combinations thereof to enable so-called distinguishable particle sets or populations as generally disclosed in U.S. Pat. No. 6,268,222.

"Receptor" is any macromolecular compound or composition capable of recognizing (e.g. such as having an enhanced binding affinity to) a particular spatial and polar organization of a molecule, i.e., epitopic or determinant site. Illustrative receptors include naturally occurring receptors, e.g., thyroxine binding globulin, antibodies, enzymes, immunoglobulin (Fab) fragments, lectins, various proteins found on the surface of cells (cluster of differentiation or CD molecules), and the like. CD molecules denote known and unknown proteins on the surface of eukaryotic cells, for example, CD4 is the molecule that primarily defines helper T lymphocytes.

"Haptens" can include naturally occurring hormones, naturally occurring drugs, synthetic drugs, pollutants, allergens, affector molecules, growth factors, chemokines, cytokines, lymphokines, amino acids, oligopeptides, chemical intermediates, nucleotides, oligonucleotides, and the like. The use for such compounds may be in the detection of drugs of abuse, therapeutic dosage monitoring, health status, donor matching for transplantation purposes, pregnancy (e.g., hCG or alpha-fetoprotein), detection of disease, e.g. endotoxins, cancer antigens, pathogens, and the like.

"Immunoconjugate" is a molecule formed by attachment of two different molecules or entities, such as an antibody (label) and a second usually biologically active molecular entity (analyte) such as an organic drug molecule, a radionuclide, an enzyme, a toxin, a protein, and like materials that can be conjugated to the antibody to form the conjugate. The antibody portion directs or guides the second molecular entity to its target enabling the second molecular entity to efficiently produce a biological or marking effect. In embodiments of the present invention immunoconjugates can include redox polymer nanoparticles.

"Drug" or "therapeutic drugs" can include, but are not limited to, anti-AIDS substances, anti-cancer substances, antibiotics, anti-viral substances, enzyme inhibitors, neurotoxins, opioids, hypnotics, antihistamines, tranquilizers, anticonvulsants, muscle relaxants and anti-Parkinson substances, anti-spasmotics and muscle contractants, miotics and anticholinergics, immunosuppressants (e.g. cyclosporins) antiglaucoma solutes, anti-parasite or anti-protozoal solutes, anti-hypertensives, analgesics, anti-pyretics and anti-inflammatory agents (such as NSAID's), local anesthetics, ophthalmics, prostaglandins, anti-depressants, anti-psychotic substances, anti-emetics, imaging agents, specific targeting agents, neurotransmitters, proteins and cell response modifiers. Proteins are of general interest in a wide variety of diagnostics, such as detecting cell populations, blood type, pathogens, immune responses to pathogens, immune complexes, saccharides, lectins, naturally occurring receptors, and the like. Receptors may find use in binding to haptens, proteins, other receptors, or the like, or detection of the presence of pathogens, the level of a particular protein in a physiological fluid, the presence of haptens in a wide variety of samples, such as physiological fluids, air, process streams, water, and the like. Nucleic acids can also be used in the detection of complementary strands, proteins specifically binding to nucleic acids, and the like.

The label entities can also be selected from fluorescent reporter molecules which are capable of reacting with a variety of inorganic analytes that define properties of biological fluids, air, water, and the like, for example, oxygen, carbon dioxide, pH, $Ca^{2+}$, $Na^+$, $K^+$, or $Cl^-$, as disclosed for example in U.S. Pat. No. 5,747,349.

Analytes of particular interest are microorganisms and cells, including viruses, prokaryotic and eukaryotic cells, unicellular and multi-cellular organism, e.g., fungi, bacterial, mammalian, etc., and fragments or components thereof. Other analytes of particular interest are pathogens. Monoclonal or polyclonal antibodies or other selective labels can be linked to the surface of a pathogens to serve as catching antibodies. The sample can then be added and cells having the epitope recognized by the antibody bind to the antibody on the surface. Non-specifically bound pathogens are washed away leaving substantially only specifically bound ones. Labeled monoclonal antibodies are then added which are specific for an epitope other than the epitope recognized by the catching antibody. "Epitope" is synonymous with antigenic determinant and can be a defined domain on the molecule that serves as a reaction or binding site. A molecule may have one or more epitopes. For example, a first epitope can enable coupling of a target analyte with a first label and second epitope can provide a binding site or domain for a second label on the target analyte.

Pathogens of interest can be, for example, viruses such as Herpesviruses, Poxviruses, Togaviruses, Orthomyxoviruses, Paramyxoviruses, Rhabdoviruses, Coronaviruses, Arenaviruses, and Retroviruses. Pathogens also include bacteria including but not limited to *Escherichia coli, Pseudomonas aeruginosa, Enterobacter cloacae, Staphylococcus aureus, Enterococcus faecalis, Klebsiella pneumoniae, Salmonella typhimurium, Staphylococcus epidermidis, Serratia marcescens, Mycobacterium bovis*, methicillin resistant *Staphylococcus aureus* and *Proteus vulgaris*. A non-exhaustive list of these organisms and associated diseases can be found, for example, in U.S. Pat. No. 5,795,158.

Assays using nanoparticles of the invention can be carried out in a biological fluid, including separated or unfiltered biological fluids such as urine, cerebrospinal fluid, pleural fluid, synovial fluid, peritoneal fluid, amniotic fluid, gastric fluid, blood, serum, plasma, lymph fluid, interstitial fluid, tissue homogenate, cell extracts, saliva, sputum, stool, physiological secretions, tears, mucus, sweat, milk, semen, vaginal secretions, fluid from ulcers and other surface eruptions, blisters, abscesses, and extracts of tissues including biopsies of normal, malignant, and suspect tissues or any other constituents of the body which may contain the analyte of interest. Other similar specimens such as cell or tissue culture or culture broth are also of interest. Alternatively, the sample can be obtained from an environmental source, such as soil, water, or air; or from an industrial source such as taken from a waste stream, a water source, a supply line, or a production lot. Industrial sources also include fermentation media, such as from a biological reactor or food fermentation process such as brewing; or foodstuff, such as meat, game, produce, or dairy products. The test sample can be pre-treated prior to use, such as preparing plasma from blood, diluting viscous fluids, and the like; methods of pre-treatment can involve filtration, fractionation, distillation, concentration, inactivation of interfering compounds, and addition of reagents, and like steps, or combinations thereof.

Methods for detecting multiple subpopulations of analytes are known, see for example, U.S. Pat. No. 5,567,627, to Lehnen, and can be adapted to the present invention. Methods for detecting a nucleic acid with one or more type of particles having oligonucleotides attached thereto including an electrochemical assay with a probe oligonucleotide having attached a redox-active molecule, such as a redox-active ferrocene derivative, for example as in U.S. Pat. No. 6,417,340, to Mirkin, et al, can be adapted to the present invention. Methods for electrochemical detection and localization of genetic point mutations and other base-stacking perturbations within oligonucleotide duplexes adsorbed onto electrodes, such as U.S. Pat. No. 6,221,586, to Barton, et al., can be adapted to the present invention. Methods for multiplexed fluorescent analysis of a plurality of analytes in a sample, such as U.S. Pat. No. 6,268,222, to Chandler, et al., can be adapted to the present invention. Other detection methods include using ultraviolet and visible spectroscopy, see for example X. Gong and E. S. Yeung, *Anal. Chem.*, 71, 4989 (1999), "An Absorption Detection Approach for Multiplexed Capillary Electrophoresis Using a Linear Photodiode Array". Methods for separating cells using a flow through fractional cell sorting process based on the application of a magnetic force to cells having a range of magnetic labeling densities, such as U.S. Pat. No. 5,968,820, to Zborowski, et al., can be adapted to the present invention. Methods for separating particles bound to each other via non-covalent binding and agglomeration, such as U.S. Pat. No. 4,279,617, to Masson et al., can be adapted to the present invention.

For the purposes of the present invention the nanoparticle's redox component should provide a signal related to the presence of analyte in the sample. Similarly, when a label is selected which includes, for example, a fluorescent component it should provide a signal related to the presence of analyte in the sample and which signal can be detected as electromagnetic radiation, particularly as radiation in the ultra-violet, visible or infrared range.

The redox nanoparticle article or its precursor component redox polymer nanoparticles and the methods of use can also be used to isolate various products of interest, such as blood plasma proteins, growth factors, clotting factors, anti-clotting factors, and the like, which may then be released entirely or in-part from the resulting complex by various salt solutions or by the redox cleavant. The redox nanoparticle article or its precursor components of the invention may be used for a variety of other purposes, for example, to selectively provide or deliver a high density of a redox active molecule to the surface of an analyte, such as in the treatment of a medical condition or disease.

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. When alkyl can be partially unsaturated, the alkyl chain may comprise one or more (e.g. 1, 2, 3, or 4) double or triple bonds in the chain.

Aryl or arenyl refers to a phenyl radical or an ortho-fused bicyclic carbocyclic radical having about nine to ten ring atoms in which at least one ring is aromatic.

Substituted aryl or substituted arenyl refers to an aryl or arenyl as defined herein which can further include one or more heteroatoms or substituents attached to the aryl, such as —OH, carboxylic acid —$CO_2H$, carboxylic acid esters —$CO_2(C_{1-7})$alkyl, —CN, nitro, $(C_{1-7})$alkoxy, $(C_{1-7})$alkyl, substituted $(C_{1-7})$alkyl, poly{substituted $(C_{1-7})$alkyl}, $(C_{1-7})$alkanoyl, aryl, substituted aryl, —$S(C_{1-7})$alkyl, —$NX(C_{1-7})$alkyl where X is —H or $(C_{1-7})$alkyl, and like substituents.

Arylalkyl or aryl$(C_{1-7})$alkyl refer to a group of the formula aryl$(C_{1-7})$alkyl-, where aryl- and $(C_{1-7})$alkyl- are as defined herein.

Substituted $(C_{1-7})$alkyl refers to a $(C_{1-7})$alkyl as defined herein which can further include one or more heteroatoms within the alkyl chain, such as —O—, —S—, —NX— where X is —H or $(C_{1-7})$alkyl, or one or more substituents attached to the alkyl chain, such as =O, =S, —OH, —$(C_{1-7})$alkoxy, —$S(C_{1-7})$alkyl, —$NX(C_{1-7})$alkyl where X is —H or $(C_{1-7})$alkyl.

The term poly{substituted $(C_{1-7})$alkyl} includes oligo-ethoxylates and oligo-proproxylates, such as —$(OCR^3CH_2)_o$—$OR^3$, where $R^3$ is —H or $(C_{1-7})$alkyl, such as —$CH_3$, and o is 1 to about 10.

Cyclo$(C_{3-7})$alkenyl refers to a divalent carbocyclic ring having 3-7 carbon atoms, such as, cyclopropyl, cyclobutyl, cyclopentyl, cyclohexyl, or cycloheptyl.

Aryl$(C_{1-7})$alkenylaryl in the context of $R^2$ refers to an radical having an aryl at each end and an alkenyl separating the aryls, for example, of the formula —$C_6H_4$—$(CH_2)_6$—$C_6H_4$—.

The term "protecting group" as used herein are known to those skilled in the art, for example, acetyl or benzyloxycarbonyl, $(C_{1-7})$alkyl, phenyl or benzyl ester or amide, and like groups, see for example, T. W. Greene, *Protecting Groups In Organic Synthesis*; Wiley: New York, 1981, and references cited therein.

"Partially unsaturated", for example, a $C_{1-7}$alkyl which is optionally partially unsaturated, means the named substituent has one or more unsaturations, such as one or more double bonds, one or more triple bonds, or both.

"Optional" or "optionally" mean that the subsequently described event or condition may but need not occur, and that the description includes instances where the event or condition occurs and instances in which it does not. For example, "optionally substituted" means that the named substituent may be present but need not be present, and the description includes situations where the named substituent is included and situations where the named substituent is not included.

The terms "include", "for example", "such as", and the like are used illustratively and are not intended to limit the present invention.

The indefinite articles "a" and "an" mean "at least one" or "one or more" when used in this application, including the claims, unless specifically indicated otherwise.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine, for example, therapeutic activity using the standard tests or other similar tests which are known in the art.

Specific and preferred values herein for radicals, substituents, and ranges, are for illustration only; they do not exclude other defined values or other values within defined ranges for the radicals and substituents. The compounds of the invention include polymers of formula (I) having any combination of the values, specific values, more specific values, and preferred values described herein.

Specifically, $C_{1-7}$alkyl can be methyl, ethyl, propyl, isopropyl, butyl, iso-butyl, sec-butyl, pentyl, 3-pentyl, hexyl, or heptyl; $C_{1-7}$alkoxy can be methoxy, ethoxy, propoxy, isopropoxy, butoxy, iso-butoxy, sec-butoxy, pentoxy, 3-pentoxy, hexyloxy, 1-methylhexyloxy, or heptyloxy; $C_{1-7}$alkanoyl can be acetyl, propanoyl, butanoyl, pentanoyl, 4-methylpentanoyl, hexanoyl, or heptanoyl; aryl can be phenyl, indenyl, or naphthyl.

When $C_{1-7}$alkyl is unsaturated or partially unsaturated, it can specifically be vinyl, allyl, 1-propenyl, 2-propenyl, 1-butenyl, 2-butenyl, 3-butenyl, 1,3-butadienyl, 1-pentenyl, 2-pentenyl, 3-pentenyl, 4-pentenyl, 1-hexenyl, 2-hexenyl, 3-hexenyl, 4-hexenyl, 5-hexenyl, ethynyl, 1-propynyl, 2-propynyl, 1-butynyl, 2-butynyl, 3-butynyl, 1-pentynyl, 2-pentynyl, 3-pentynyl, 4-pentynyl, 5-hexene-1-ynyl, 2-hexynyl, 3-hexynyl, 4-hexynyl, or 5-hexynyl.

A specific value for $R^1$ is absent, that is where m is 0.

Another specific value for $R^1$ is poly{substituted ($C_{1-7}$) alkyl}.

Another specific value for $R^1$ is substituted ($C_{1-7}$)alkyl of the formula —(OCR$^3$CH$_2$)$_o$—OR$^3$, where $R^3$ is —H or —CH$_3$, and o is 1 to about 10.

Another specific value for $R^1$ is —(OCR$^3$CH$_2$)$_o$—OR$^3$, where $R^3$ is —H or —CH$_3$, and o is 1 to about 10.

A specific value for $R^2$ is hexenyl.

Another specific value for $R^2$ is substituted ($C_{1-7}$) alkenyl or poly{substituted ($C_{1-7}$) alkenyl} of the formula —(OCR$^3$CH$_2$)$_p$—, where $R^3$ is —H or ($C_{1-7}$) alkyl or ($C_{2-7}$) alkylenyl, and p is 1 to about 50. Examples of $R^2$ as a poly{substituted ($C_{1-7}$) alkenyl} can be prepared from commercially available poly(alkylene) oxides or poly(alkylene) glycols, such as poly(propylene) glycol, or by known polyalkoxylation methods.

A specific value for m is 0.

Another specific value for m is 1.

A specific value for n is from about 10 to about 1,000.

Another specific value for n is from about 10 to about 500.

Another specific value for n is from about 10 to about 100.

Preferred compounds of the invention are, for example, polymers of the formula (II):

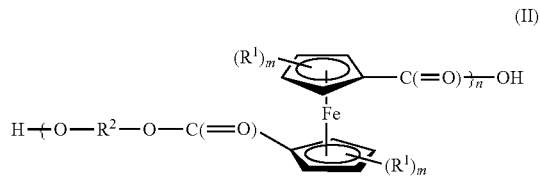

(II)

wherein $R^1$ is substituted ($C_{1-7}$)alkyl of the formula —(OCR$^3$CH$_2$)$_o$—OR$^3$, where $R^3$ is —H or —CH$_3$, and o is 1 to about 10; $R^2$ is ($C_{1-7}$)alkenyl, for example, as hexenyl or poly{substituted ($C_{1-7}$) alkenyl}, such as poly(propylene) glycol with from 2 to about 25 propylene oxide units; m is 1, and n is about 10 to about 500; or salts thereof.

More preferably, the polymers of the invention are of the formula (II) wherein $R^2$ is hexenyl; and n is 10 to about 100; or salts thereof. Other preferred compounds of the invention are, for example, polymers of the formula (II) wherein the hydroxy end groups or other hydroxy substituents are converted to suitable protecting groups or bonded to label or analytes, and which groups can be readily and selectively removed if desired, and which groups can impart additional useful stability or functionality to the nanoparticles, for example, including a fluorophore or an magnetophore.

In cases where the redox polymers are sufficiently basic or acidic to form stable acid or base salts, preparation of the polymers as salts may be appropriate. Examples of acceptable salts are organic acid addition salts formed with acids which form a acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts. Acceptable salts may be obtained using standard procedures known in the art, for example by reacting a sufficiently basic compound such as an amine with a suitable acid affording a diagnostically acceptable anion. Alkali metal (e.g., sodium, potassium or lithium) or alkaline earth metal (e.g. calcium) salts of carboxylic acids can also be made.

The following general methodologies were employed in preparing and evaluating compounds, polymers, particles, and conjugates or adducts, of the present invention.

Preparation of Poly(1,1'-dihexylferrocenyl)ester (PDE) nanoparticles

As shown in Scheme I, a one-pot preparation of PDE nanoparticles was accomplished by combining a difunctional ferrocene compound, such as ferrocene dicarboxylic acid, with difunctional spacer compound, such as 1,6-hexane diol, in the presence of an acid catalyst, such as para-toluene sulfonic acid, and in the presence of a suitable emulsifier or surfactant, such as sodium dodecylsulfate.

Scheme I

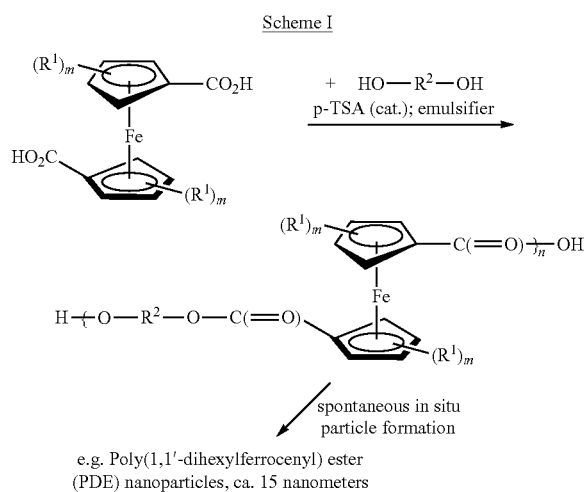

e.g. Poly(1,1'-dihexylferrocenyl) ester
(PDE) nanoparticles, ca. 15 nanometers

The di-functional ferrocene compound can be optionally substituted with additional $R^1$ substituents (e.g. where m is 1, 2, 3 or 4) to provide molecular or particulate control features, for example, providing either or both sterically bulky groups and solubilizing groups which can change, for example, the relative hydrophobicity, dissolution and partition properties, and geometry of the soluble or crystalline polymer or its particulates in various pure or mixed solvents or in close biological environments, such as, in or on membranes or receptor binding sites. The selection of the $R^1$ substituents can also be used to control or alter the redox properties of the particles. Similarly, the difunctional spacer compound reactant, such as HO—$R^2$—OH, can be selected for reactivity, solubility, chain length, steric, and like properties, to further tailor the features of the resulting polymer and its nanoparticles. The $R^1$ substituents and difunctional spacer compound can also be selected to contain functional groups, such as, reactive groups or protected groups, which can be used to introduce, for example, additional complexation sites or fluorophores that can enhance or supplement labeling and detection schemes in target analyte systems.

The invention will now be illustrated by the following non-limiting examples:

Example 1

Preparation of Poly(1,1'-dihexylferrocenyl)ester (PDE) Nanoparticles. A mixture of 0.04 mmol ferrocene dicarboxylic acid (FDA), 0.084 mmol 1,6-hexanediol, and 0.1 mol percent p-toluene sulfonic acid in 100 mL of 10 mM sodium phosphate buffer (pH=7.2) containing 4 mM sodium dodecylsulfate (SDS) surfactant was stirred until an emulsion resulted. The emulsion was then heated at 80° C. for 30 minutes with gentle stirring and allowed to cool. The resulting mixture was separated by simple filtration and the readily filterable redox polymer (nanoparticle) particulate product was characterized further and as described below. Alternatively, the resulting mixture could be used directly as a source of redox polymer nanoparticles.

Preparation of Copolyester(1,6-dicarboxy hexane, 3,3'-diol ferrocene) Nanoparticles. In an alternative preparative procedure the related copolyester of a dicarboxy spacer compound, such as 1,6-hexane dicarboxylic acid, and a dihydroxy ferrocene compound such as 3,3'-dihydroxy ferrocene, is prepared by combining approximately equimolar amounts of the ferrocene diol, and the dicarboxylic acid spacer compound, and 0.1 mol percent p-toluene sulfonic acid catalyst in 100 mL of 10 mM sodium phosphate buffer (pH=7.2) containing 4 mM sodium dodecylsulfate (SDS) surfactant to form an emulsion. The emulsion is heated at 80° C. for 30 minutes with gentle stirring and allowed to cool. The resulting mixture can be separated by simple filtration, or alternatively, by known nano-filtration methods, and the readily filterable redox polymer (nanoparticle) particulate product can be characterized further and as described below. Alternatively, the resulting mixture could be used directly as a source of redox polymer nanoparticles.

Example 2

PDE Nanoparticle Label Attachment, Disintegration, and Detection Referring to FIG. 1A, there is schematically illustrated an example of the labeling method and method of making the nanoparticle article of the present invention. A sample containing a mixture of analytes, including a target analyte (10), such as infectious cells, and a similar but non-identical analyte(s) (20), such as non-infectious cells, is incubated with a solution containing a selective label (30), such as an antibody or aptamer. The label selectively attaches to the target analyte to form a labeled-analyte (35) adduct or conjugate. The label can be tagged with redox polymer nanoparticles (40) either before or after the label is exposed to the sample mixture. The resulting combined nanoparticle-label-analyte (45) conjugate provides a surface on a target analyte, such as a micro-organism or cell component, which is selectively decorated with a label component and a redox polymer nanoparticle component. In embodiments, the similar but non-identical analyte(s) (20) can optionally be separated if desired from either the labeled-analyte (35) or the combined redox polymer nanoparticle-labeled-analyte (45).

Figure 1B:
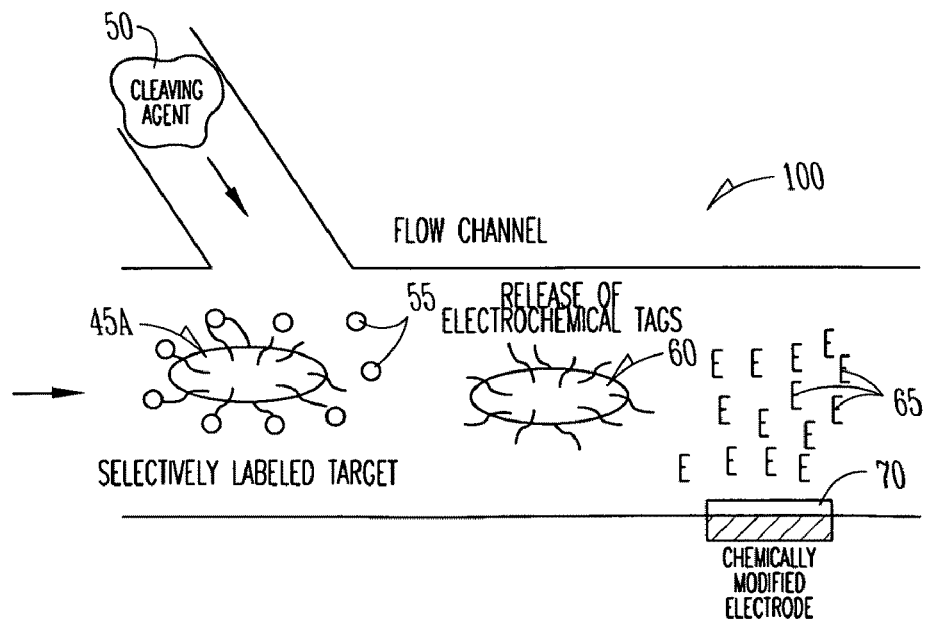
FIG. 1B schematically illustrates an example of the detection method and apparatus of the present invention.

Referring to FIG. 1B, there is schematically illustrated an example of the integrated detection method and apparatus of the present invention and referred to, respectively, as electrochemical flow cytometry and electrochemical flow cytometer. The apparatus includes two interconnected microfluidic flow channels and a chemically modified electrode (70). One flow channel carriers the nanoparticle-labeled-analyte (45a) stream while a second flow channel carries a redox cleavant (50), such as a continuous stream or a controllable intermittent feed injected into a continuous carrier stream. The channels are configured to permit convergence of the respective streams so that the redox cleavant can act on the nanoparticle-label-analyte to liberate either or both nanoparticles (55) and nanoparticle redox products or components "E"(65), and to regenerate a label-analyte entity (60) at a location just prior to, or in the vicinity of, the chemically modified electrode (70). The surface associated or surface bound redox polymer nanoparticles in the nanoparticle-label-analyte (45) provide concentrated packets of a redox-active species "E"(65). In an example of the electrochemical flow cytometry method a sample containing the nanoparticle-label-analyte (45) is injected into a first flow channel of the flow cytometer (100) that mixes with a stream of redox cleavant (cleaving agent) which breaks down or disintegrates the nanoparticle portion of the conjugate into its redox component(s) such as redox detectable specie(s) "E". The resulting concentrated plug or bloom of redox component(s) (65) can be detected at a point or points down stream using, for example, amperometry in a threshold detection mode and a chemically modified electrode (70). The chemically modified electrode, or other similar or equivalent electrodes, provide a way to manipulate the electrode surface properties to enhance both its selectivity and sensitivity, and to minimize electrode fouling.

Example 3

Figure 2:
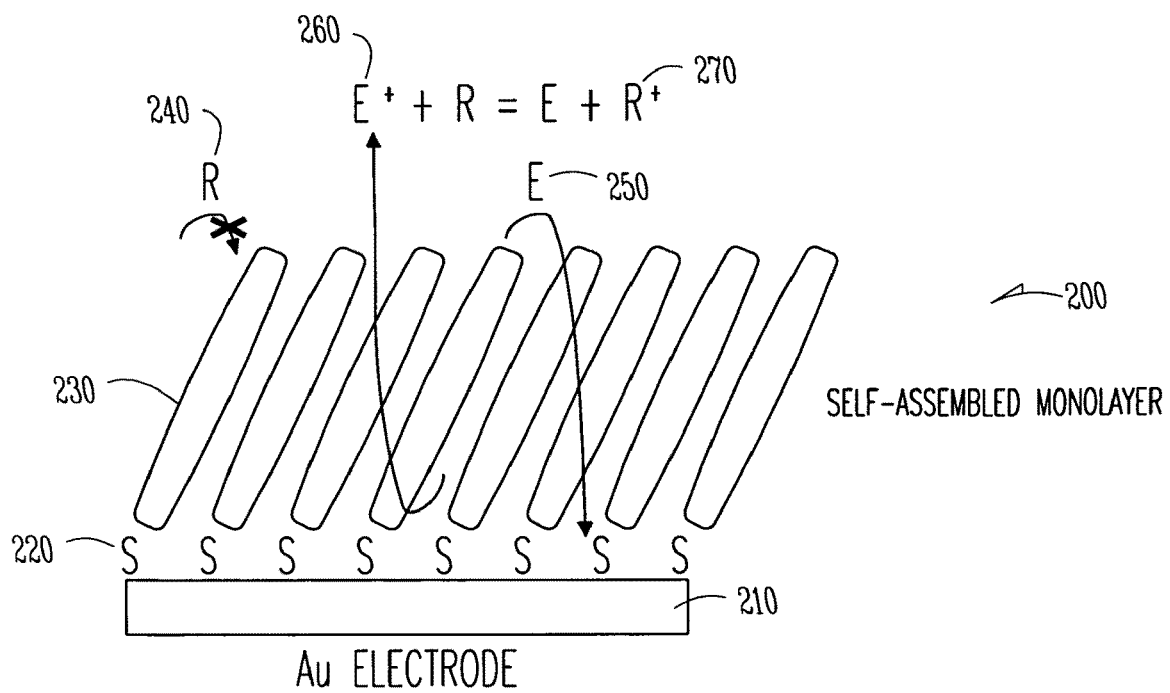
FIG. 2 schematically illustrates aspects of enhanced signal transduction of the present invention using a surface modified electrode.

Redox Polymer Nanoparticle Adduct-Redox Component Signal Detection and Amplification Referring to FIG. 2, there is illustrated, although not wanting to be limited by theory, aspects of enhanced signal transduction and detection of the present invention which can be accomplished by amplifying the electrochemical signal response, for example, using a surface modified electrode, and by generating a high local concentration of a detectable redox component in the vicinity of the surface modified electrode. An electrode (210) can be coated with, for example, a self-assembled mono-layer (230) which layer acts as a selective barrier to heterogeneous electron transfer. For example, it is known that a surface modified gold electrode (200) having a bound monolayer of dodecanethiolate (220/230) blocks (indicated by the arrow line with X) electrolysis of the hydrophilic species (R)(240), such as $Fe(CN)_6^{4-}$, but only marginally suppresses the electrolysis of the hydrophobic species (E)(250), such as hydroxymethylferrocene. If both hydrophilic and hydrophobic species are present in solution, the current for the oxidation of E to $E^+$ is amplified by the regeneration of E by the homogenous reaction of $E^+$ (260), with the reduced form of R (240), which is oxidized to $R^+$ (270). The magnitude of the amplification can be controlled by, for example: 1) the rates of both heterogeneous and homogenous reactions, and 2) the thermodynamic driving force for the homogenous reaction between $E^+$ and R. Generating a high local concentration of redox component E in the vicinity of the surface modified electrode is accomplished by selective degradation of the redox polymer nanoparticle component of the redox polymer nanoparticle-label-analyte adduct with the redox cleavant. The combination of selective liberation of the redox component E and the enhanced electrode sensitivity due to amplification produces a large signal which can be easily distinguished from, for example, a signal arising from the redox component of residual unbound redox polymer nanoparticles.

Some of the limitations of known immunolabel and recognition schemes can be overcome with improved molecular recognition ligands or labels in combination with or including the redox polymer nanoparticles of the present invention. Examples of improved molecular recognition ligands or labels of the present invention are aptamers which are oligomeric nucleic acids, typically with about 20 to about 100 base pairs in length, and isolated from pools of oligomers with random sequences. Through iterative processes known as SELEX (systematic evolution of ligands by exponential enrichment) and counter-SELEX, which involve a series of binding affinity steps and PCR amplification, oligonucleotides with high affinity and specificity for a target analyte can be isolated according to known procedures. Since aptamers can be readily and reproducibly prepared in the laboratory, often with the aid of automation, complications or shortcomings of using antibodies, for example, binding diversity, sample matrices, and small molecule binding, can be notably reduced or avoided.

Example 4

Figure 3A:
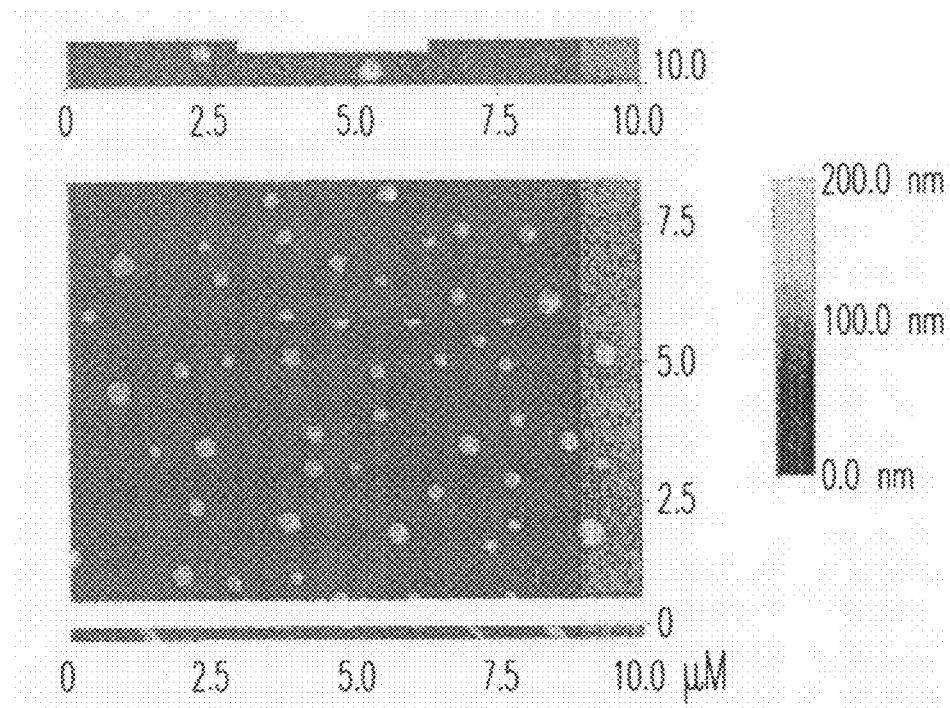
FIG. 3A illustrates topographic images obtained from tapping-mode atomic force microscopy (TM-AFM) characterization of redox polymer nanoparticles on a silicon substrate in embodiments of the present invention.
Figure 3B:
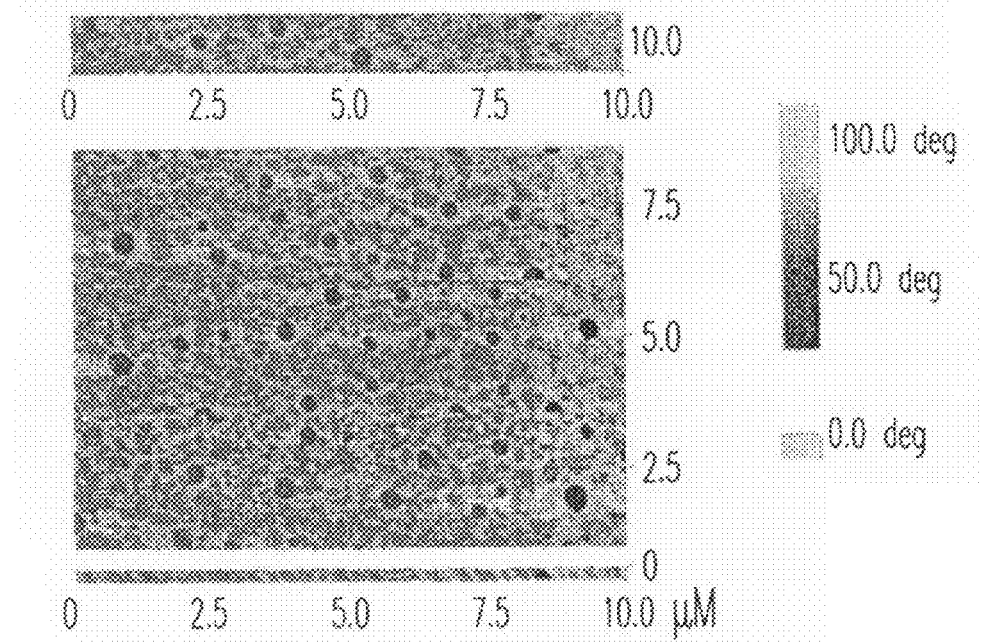
FIG. 3B illustrates phase images obtained from TM-AFM characterization of redox polymer nanoparticles on a silicon substrate in embodiments of the present invention.
Figure 4A:
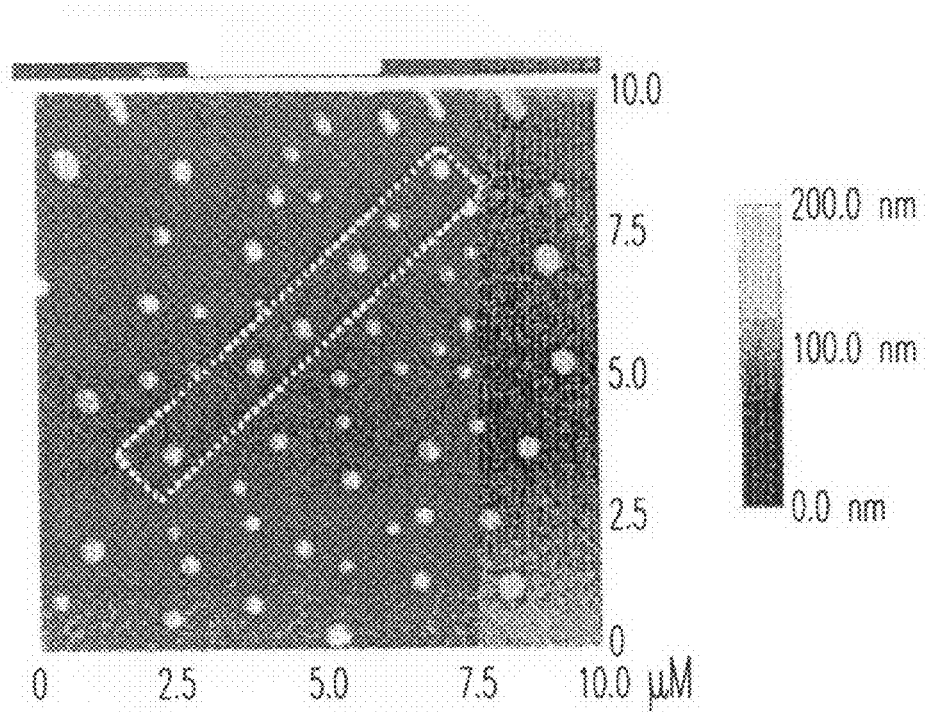
FIG. 4A illustrates a cross-sectional analysis of TM-AFM topographic images of FIG. 3A in embodiments of the present invention.
Figure 4B:
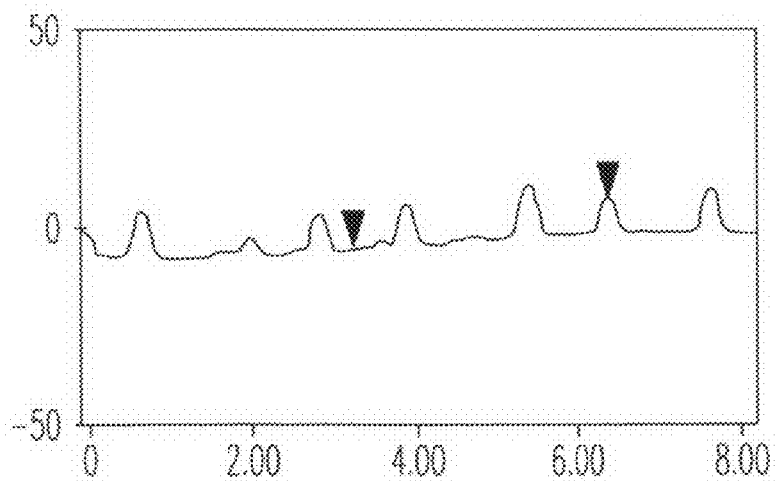
FIG. 4B illustrates typical particle size characterization of redox polymer nanoparticles in embodiments of the present invention.

Tapping-Mode Atomic Force Microscopy (TM-AFM) Characterization of PDE Nanoparticles. Samples of PDE nanoparticles for TM-AFM were prepared by spin-coating a clean 1 cm×1 cm silicon wafer with several drops, such as 0.2 mL, of the PDE nanoparticle solution of Example 1 at 3,000 rpm for 60 seconds. The coated wafer was rinsed with ethanol then dried under a directed stream of high purity nitrogen. Referring to FIG. 3A there is shown "height images" obtained from the tapping-mode atomic force microscopy (TM-AFM) characterization of PDE nanoparticles on the silicon substrate. Referring to FIG. 3B there is shown the corresponding "phase images" obtained from tapping-mode atomic force microscopy (TM-AFM) characterization of PDE nanoparticles on the silicon substrate. Referring to FIG. 4A there is illustrated a cross-sectional analysis of TM-AFM "height images" of FIG. 3A in embodiments of the present invention. Referring to FIG. 4B there is illustrated a typical particle size characterization of redox polymer nanoparticles in embodiments of the present invention.

Example 5

Figure 5:
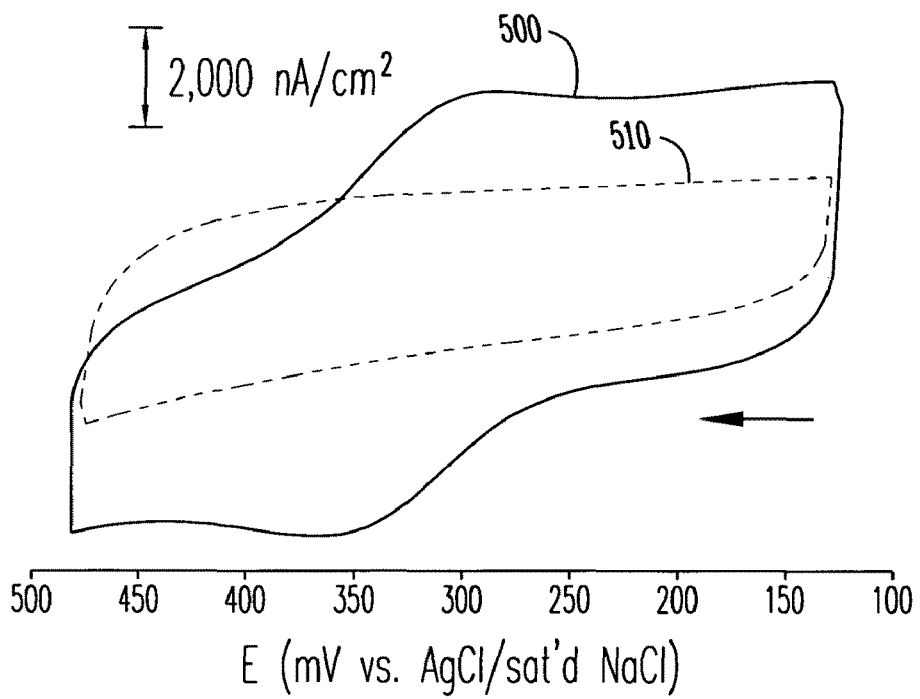
FIG. 5 is a cyclic voltammetry characterization of redox polymer nanoparticles in embodiments of the present invention.

Cyclic Voltammetry (CV) Characterization of PDE Nanoparticles. Referring to FIG. 5, there is illustrated cyclic voltammetry properties observed in the characterization of PDE nanoparticles of the present invention compared to a background scan. CV experiments were performed at a 3 mm gold disc working electrode (Bioanalytical Systems, polished with 0.3 micron alumina just before use) with a platinum (Pt) coil as the auxiliary electrode and an Ag/AgCl/saturated KCl reference electrode. The volume of the phosphate-buffered surfactant solution containing the sample was reduced by half to concentrate the PDE nanoparticle containing nanoparticle sample (500) obtained from the preparative Example 1. For comparison, a background scan (510) was taken of a blank phosphate-buffered surfactant solution after reducing the solution volume by one-half. Scans were initiated at +125 mV and reversed at +475 mV. The scan rate was 100 mV per second. Noteworthy features of the cyclic voltammogram include: 1) only one reversible redox wave which indicates that the exposed ferrocene groups are in the same or similar electrochemical environment and which feature agrees with reported electrochemistry of micelle-solubilized ferrocenes (see Vives-Rego, et al., FEMS Microbiol. Rev., 24, 429 (2000); Jayasena, S. D., et al., Clin. Chem., 45, 1628-1650 (1999); Szostak, J. W. and Ellington, A. D., Nature, 346, 818-822 (1990); and Gold, L. and Tuerk, C., Science, 249, 505-510 (1990)); and 2) the standard reduction potential of the couple is about 339 millivolts, which is similar to that of ferrocene dicarboxylic acid (FDA) in aqueous solutions.

Example 6

Figure 6:
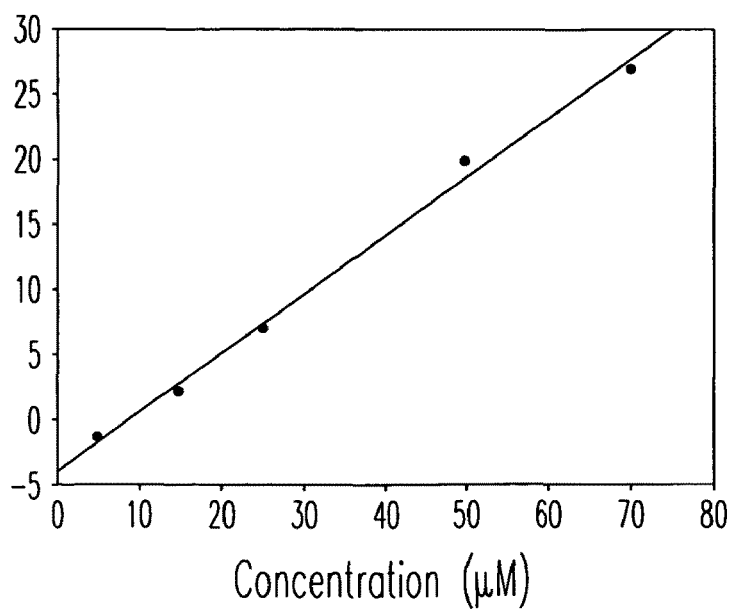
FIG. 6 is a calibration curve of reference sample solutions containing redox polymer nanoparticles of known sizes in embodiments of the present invention.

Spectrophotometric Characterization of PDE Nanoparticles. The concentration of one 15 nanometer PDE nanoparticle was estimated spectroscopically by determining the amount of iron (II) present in solution according to a known procedure (see Gold, L., et al., Curr. Opin. Genet. Dev., 7, 848-851 (1997); and Gold, L., et al., Proc. Nat'l. Acad. Sci. USA, 94, 59-64 (1997)). The amount of iron (II) is determined by heating any ferrocene-based compound in a solution of 5 percent trichloroacetic acid (TCA). Iron (II) is quantified by monitoring the formation of the iron (II) ferrozine complex at 564 nanometers. To compare the quantity of ferrocene present in a PDE nanoparticle, a calibration curve was constructed using the aforementioned procedure and ferrocene dicarboxylic acid (FDA) as the reference analyte. FIG. 6 provides a typical calibration curve for five solutions with different concentrations of ferrocene dicarboxylic acid (FDA) in a phosphate buffer containing surfactant. A solution from Example 1 of PDE nanoparticles was treated identically, and after extrapolation from the calibration curve, the concentration of ferrocene in a 6 mL sample was about 53.7 micro-molar. This concentration can be used to estimate the number of PDE nanoparticles per mL solution, $N_{PDE}$, as follows. The number of ferrocene units per nanoparticle is first estimated based on relative volumes. Using two solid cones, each with a radius, r=1.389 Angstroms and height, h=1.485 Angstroms (see Gold, L., et al., *Nucleic Acids Res.*, 25, 781-786 (1997)), to define the ferrocenyl group geometry, the volume of a ferrocenyl group is calculated to be $V_{FC}$=6.00 cubic Angstroms or $6.00 \times 10^{-2}$ cubic nanometers. To simplify the calculation, it is assumed that all of the PDE nanoparticles are spherical, and have a diameter, d=15 nanometers, based on the aforementioned cross-section analysis of AFM height images. Therefore, the volume of one PDE nanoparticle is $V_{np}=1.77 \times 10^3$ cubic nanometers. Dividing $V_{np}$ by $V_{Fc}$ results in $N_{Fc1}$, the number of ferrocene units in one PDE nanoparticle according to:

$$N_{Fc1} = V_{np}/V_{Fc}.$$

For a single 15 nanometer particle, $N_{Fc1} = 2.95 \times 10^5$ ferrocene units. If a ferrocene concentration of 53.7 micromolar in a sample volume of 6 mL (determined spectrophotometrically) is selected, then the number of ferrocene molecules in this volume, $N_{Fc2}$, can be calculated to be $N_{Fc2}=1.94 \times 10^{17}$. The number of 15 nanometer particles, $N_{15}$ is given by $N_{15}=N_{Fc2}/N_{Fc1}$ or $N_{15}=6.58 \times 10^{11}$ 15 nanometer particles. Finally, $N_{PDE}$ can be calculated by dividing $N_{15}$ by the solution volume from the spectrophotometric data, giving $N_{PDE} = \frac{1}{10} \times 10^{14}$ PDE nanoparticles per milliliter of solution. This value is of similar magnitude for many commercially available polystyrene nanoparticles prepared by a similar emulsion polymerization strategy.

All publications, patents, and patent documents are incorporated by reference herein, as though individually incorporated by reference including: Murray, R. W., "Chemically Modified Electrodes," *Electroanalytical Chemistry*, A. J. Bard, Ed. Marcel Dekker, New York, N.Y. 1984, p. 191-368; Creager, S. E., et al., *Anal. Chem.*, 71, 5101-5108 (1999); Tondra, M., et al., *J. Vac. Sci. Technol. A.*, 18, 1125-1129 (2000); Tondra, M., et al., *IEEE Transactions on Magnetics*, 37, 2621-2623 (2001); and Szostak, J. W. and Wilson, D. S., *Annu. Rev. Biochem.*, 68, 611-647 (1999). The invention has been described with reference to various specific and preferred embodiments and techniques. However, it should be understood that many variations and modifications may be made while remaining within the spirit and scope of the invention.

What is claimed is:

1. A conjugate comprising a nanoparticle associated with an analyte, wherein the nanoparticle comprises a polymer that comprises two or more redox-active species, the redox-active species comprises a disubstituted metallocene, and the metallocene is directly substituted by at least one oxygen, carbonyl, nitrogen, or vinyl group.

2. The conjugate of claim 1 wherein the nanoparticle is associated with the analyte adsorptively, covalently, ionically, hydrophobically, or by hydrogen bonding.

3. The conjugate of claim 2 wherein the nanoparticle and the analyte are covalently bonded either directly or through a linking group.

4. The conjugate of claim 1 wherein the polymer of the nanoparticle comprises one or more units of formula (III):

$$-D-R^2-D-Ar(R^1)_m-M-Ar(R^1)_m- \quad (III)$$

wherein:
M is a complexed metal atom or metal ion;
Ar is unsubstituted or substituted arenyl or aromatic group complexed to M each $R^1$ is independently an arenyl substituent or aromatic substituent selected from —OH, $(C_{1-7})$alkoxy, $(C_{1-7})$alkyl, substituted $(C_{1-7})$alkyl, poly[substituted $(C_{1-7})$alkyl], $(C_{1-7})$alkanoyl, aryl, —$(OCR^3CH_2)_o$—, or substituted aryl;

$R^2$ is $(C_{1-7})$alkenyl, substituted $(C_{1-7})$ alkenyl, poly[substituted $(C_{1-7})$ alkenyl], cyclo$(C_{3-7})$alkenyl, aryl$(C_{1-7})$alkenyl, $(C_{1-7})$alkenylaryl, —$(OCR^3CH_2)_p$—, or aryl$(C_{1-7})$alkenylaryl;

each D is independently —O—, —OC(=O)—, —C(=O)O—, —NR$_a$C(=O)—, —C(=O)NR$_a$—, —OC(=O)O—, —NR$_a$C(=O)NR$_a$—, —OC(=O)NR$_a$—, —NR$_a$C(=O)O—, —C(=O)—OC(=O)—CH$_2$CH$_2$—, or —CH=CH—;

each $R_a$ is independently H or $(C_{1-7})$alkyl;
m is independently 0, 1, 2, 3, or 4;
each $R^3$ is independently —H or $(C_{1-7})$ alkyl;
o is 1 to about 10; and
p is 1 to about 50.

5. The conjugate of claim 4 wherein one or more formula (III) have the formula:

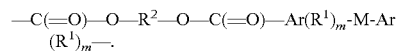

6. The conjugate of claim 4 wherein one or more formula (III) have the formula:

7. The conjugate of claim 4 wherein —Ar($R^1$)$_m$-M-Ar ($R^1$)$_m$— is a divalent ferrocene.

8. The conjugate of claim 1 wherein the polymer of the nanoparticle comprises one or more units formula (II):

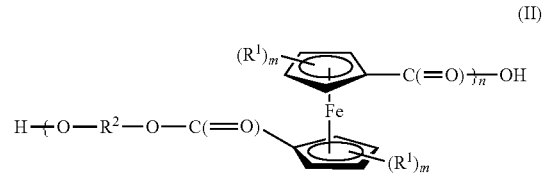

wherein:
$R^1$ is —$(OCR^3CH_2)_o$—$OR^3$, where $R^3$ is —H or —CH$_3$, and o is 1 to about 10; $R^2$ is $(C_{1-7})$alkenyl; m is 1, and n is about 10 to about 500.

9. A conjugate comprising a nanoparticle associated with a labeled-analyte, wherein the nanoparticle comprises a polymer that comprises two or more redox-active species, the redox-active species comprises a disubstituted metallocene, and the metallocene is directly substituted by at least one oxygen, carbonyl, nitrogen, or vinyl group.

10. The conjugate of claim 9 wherein the nanoparticle is associated with the labeled-analyte adsorptively, covalently, ionically, hydrophobically, or by hydrogen bonding.

11. The conjugate of claim 10 wherein the nanoparticle and the analyte are covalently bonded either directly or through a linking group.

12. The conjugate of claim 9 wherein the label of the labeled-analyte comprises a cell component, a biopolymer, a synthetic polymer, an antigen, an antibody, a receptor, a hapten, an enzyme, a hormone, a drug, a pathogen, or a toxin.

13. The conjugate of claim 9 wherein the analyte of the labeled-analyte comprises a microorganism, a virus, a cell, a cell component, a biopolymer, a synthetic polymer, an antigen, an antibody, a receptor, a hapten, an enzyme, a hormone, a drug, a pathogen, or a toxin.

14. The conjugate of claim 9 wherein the label is attached to the analyte and the nanoparticle is attached to the label, or the label and the nanoparticle are both attached to the analyte.

15. The conjugate of claim 9 wherein the nanoparticle is attached to the analyte covalently.

16. The conjugate of claim 9 wherein the polymer of the nanoparticle comprises one or more units of formula (III):

(III)

wherein:

M is a complexed metal atom or metal ion;

Ar is unsubstituted or substituted arenyl or aromatic group complexed to M each $R^1$ is independently an arenyl substituent or aromatic substituent selected from —OH, $(C_{1-7})$alkoxy, $(C_{1-7})$alkyl, substituted $(C_{1-7})$alkyl, poly[substituted $(C_{1-7})$alkyl], $(C_{1-7})$alkanoyl, aryl, —$(OCR^3CH_2)_o$—, or substituted aryl;

$R^2$ is $(C_{1-7})$alkenyl, substituted $(C_{1-7})$ alkenyl, poly[substituted $(C_{1-7})$ alkenyl], cyclo$(C_{3-7})$alkenyl, aryl$(C_{1-7})$alkenyl, $(C_{1-7})$alkenylaryl, —$(OCR^3CH_2)_p$—, or aryl$(C_{1-7})$alkenylaryl;

each D is independently —O—, —OC(=O)—, —C(=O)O—, —$NR_aC(=O)$—, —$C(=O)NR_a$—, —OC(=O)O—, —$NR_aC(=O)NR_a$—, —$OC(=O)NR_a$—, —$NR_aC(=O)O$—, —C(=O)—OC(=O)—CH$_2$CH$_2$—, or —CH=CH—;

each $R_a$ is independently H or $(C_{1-7})$alkyl;

m is independently 0, 1, 2, 3, or 4;

each $R^3$ is independently —H or $(C_{1-7})$ alkyl;

o is 1 to about 10; and p is 1 to about 50.

17. The conjugate of claim 9 wherein the nanoparticle redox-active species comprises Fe(II).

18. The conjugate of claim 9 wherein the nanoparticle comprises a poly(1,1'-dihexylferrocenyl)ester.

19. The conjugate of claim 9 wherein the polymer is selected from polystyrene, halogenated polystyrene, polyacrylic acid, polyacrylonitrile, polyamide, polyacrylamide, polyacrolein, polybutadiene, polycaprolactone, polycarbonate, polyester, polyethylene, polyethylene terephthalate, polydimethylsiloxane, polyisoprene, polyurethane, polyvinylacetate, polyvinylchloride, polyvinylpyridine, polyvinylbenzylchloride, polyvinyltoluene, polyvinylidene chloride, polydivinylbenzene, polymethylmethacrylate, polylactide, polyglycolide, poly(lactide-co-glycolide), polyanhydride, polyorthoester, polyphosphazene, polyphosophaze, polysulfone, mixtures thereof, and copolymers thereof.

20. The conjugate of claim 9 wherein redox-active species comprises one or more metals or metal ions of Cu, Ag, Au, Sn, Fe, Ni, Ru, Ti, Ta, Nb, Hf, W, Y, Zn, Zr, Al, La, Ce, Pr, Nd, Sm, Sb, Bi, Pb, Tl, In, Te, Cr, V, Mn, Mo, Co, Rh, Pd, Pt, Cd, Os, Re, Ir, or Hg.

* * * * *

UNITED STATES PATENT AND TRADEMARK OFFICE
CERTIFICATE OF CORRECTION

| | |
|---|---|
| PATENT NO. | : 7,893,177 B1 |
| APPLICATION NO. | : 11/930885 |
| DATED | : February 22, 2011 |
| INVENTOR(S) | : Marc D. Porter et al. |

It is certified that error appears in the above-identified patent and that said Letters Patent is hereby corrected as shown below:

Title Page, in "Primary Examiner", in column 2, line 1, delete "Llng-Siu" and insert -- Ling-Siu --, therefor.

In column 2, line 42, delete "nanopartical" and insert -- nanoparticle --, therefor.

In column 2, line 44, delete "nanopartical" and insert -- nanoparticle --, therefor.

In column 2, line 49, delete "nanopartical" and insert -- nanoparticle --, therefor.

In column 2, line 52, delete "nanopartical" and insert -- nanoparticle --, therefor.

In column 5, lines 10-22, delete "The redox-active species can be dispersed through the polymer matrix, can be appended to the backbone of the polymer, or can be incorporated directly into a polymer backbone. When the redox-active species is appended to the polymer it can be bonded to the polymer as a side chain or side group, but is not part of the polymer backbone. Preferably, the agent is bonded to the polymer through a linkage that is suitable to release the agent when desired. For example, it can be bonded through a group that includes a linkage that can broken by thermal, chemical, or photolytic means. For example, the redox-active species can conveniently be linked to the polymer through a hydralyzable linkage." and insert the same on Col. 5, Line 11 as a new paragraph.

In column 5, line 45, after "formula (I)" insert -- : --.

In column 6, line 52, delete "Feiser and Feiser," and insert -- Fieser and Fieser, --, therefor.

In column 6, line 58, delete "York," and insert -- York. --, therefor.

In column 14, line 22, delete "Ti," and insert -- Tl, --, therefor.

Signed and Sealed this
Seventeenth Day of May, 2011

David J. Kappos
*Director of the United States Patent and Trademark Office*

CERTIFICATE OF CORRECTION (continued)
U.S. Pat. No. 7,893,177 B1

In column 18, line 48, delete "oligo-proproxylates," and insert -- oligo-propoxylates, --, therefor.

In column 20, line 44, delete "tartarate." and insert -- tartrate, --, therefor.

In column 21, line 51, delete "1,6-hexandiol," and insert -- 1,6-hexanediol, --, therefor.